United States Patent
Mooney et al.

(10) Patent No.: US 6,592,544 B1
(45) Date of Patent: Jul. 15, 2003

(54) VASCULAR ACCESS DEVICES HAVING HEMOSTATIC SAFETY VALVE

(75) Inventors: Charles R. Mooney, Costa Mesa, CA (US); Clifford E. Currier, Aliso Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/450,032

(22) Filed: Nov. 24, 1999

(51) Int. Cl.[7] ................................................. A61M 3/00
(52) U.S. Cl. ........................................... 604/43; 604/35
(58) Field of Search .............................. 604/30, 31, 35, 604/43, 99.03, 164.04, 164.12, 164.13, 167.01, 167.03

(56) References Cited

U.S. PATENT DOCUMENTS

| | | | |
|---|---|---|---|
| 1,696,018 | A | 12/1928 | Schellberg |
| 4,299,217 | A | 11/1981 | Sagae et al. |
| 4,343,844 | A | 8/1982 | Thayer et al. |
| 4,406,656 | A | 9/1983 | Hattler et al. |
| 4,451,252 | A | 5/1984 | Martin |
| 4,601,701 | A | 7/1986 | Mueller, Jr. |
| 4,670,009 | A | 6/1987 | Bullock |
| 4,705,501 | A | 11/1987 | Wigness et al. |
| 4,758,221 | A | 7/1988 | Jureidini |

(List continued on next page.)

FOREIGN PATENT DOCUMENTS

| | | |
|---|---|---|
| DE | 30 35 243 A1 | 3/1982 |
| DE | 38 33 359 A1 | 4/1990 |
| EP | 0 000 041 B1 | 4/1981 |
| EP | 0 056 103 B1 | 1/1985 |
| EP | 0 249 456 A2 | 12/1987 |
| EP | 0 381 062 B1 | 8/1990 |
| EP | 0 495 263 A1 | 7/1992 |
| EP | 0 504 934 B1 | 9/1992 |
| EP | 0 515 119 B1 | 11/1992 |
| EP | 0 547 463 A1 | 6/1993 |
| EP | 0 593 181 A2 | 4/1994 |
| EP | 0 616 817 A1 | 9/1994 |
| EP | 0 738 520 A1 | 4/1996 |
| EP | 0 490 459 B1 | 2/1997 |
| EP | 0875262 A | 11/1998 |
| WO | WO 91/08010 | 6/1991 |
| WO | WO 92/09326 | 6/1992 |
| WO | WO 92/13584 | 8/1992 |
| WO | WO 94/00176 | 1/1994 |
| WO | WO 94/28798 | 12/1994 |
| WO | WO 95/35130 | 12/1995 |
| WO | WO 96/29111 | 9/1996 |
| WO | WO 98/23319 | 6/1998 |
| WO | WO 98/23320 | 6/1998 |
| WO | 98/24501 | 6/1998 |
| WO | WO 99/20326 | 4/1999 |

*Primary Examiner*—Manuel Mendez
(74) *Attorney, Agent, or Firm*—Lena Vinitskaya; Guy Cumberbatch

(57) ABSTRACT

A vascular access device is provided that has a device lumen valve and a safety valve feature to prevent leakage of blood from a lumen of such device. The vascular access device includes a sheath which may have an outer tube and structure defining a device lumen located therein. The access device further includes a detachable device valve which provides sealing of the device lumen. In addition, a non-detachable hemostasis safety valve is provided on the proximal end of the device lumen to seal the device lumen when no device valve is present. The device valve attaches to and simultaneously opens the proximal end of the hemostasis safety valve. In one embodiment, the device valve includes a distal projection that pierces an elastomeric valve member of the hemostasis safety valve. The elastomeric valve member of the hemostasis safety valve is stiffer than an elastomeric valve member of the device valve, and prevents introduction of guidewires and highly flexible catheters therethrough.

14 Claims, 23 Drawing Sheets

U.S. PATENT DOCUMENTS

| | | |
|---|---|---|
| 4,776,841 A | 10/1988 | Catalano |
| 4,795,439 A | 1/1989 | Guest |
| 4,842,582 A | 6/1989 | Mahurkar |
| 4,846,791 A | 7/1989 | Hattler et al. |
| 4,894,057 A | 1/1990 | Howes |
| 4,906,232 A | 3/1990 | Reynolds |
| 4,906,496 A | 3/1990 | Hosono et al. |
| 4,968,307 A | 11/1990 | Dake et al. |
| 5,021,044 A | 6/1991 | Sharkawy |
| 5,025,778 A | 6/1991 | Silverstein et al. |
| 5,053,004 A | 10/1991 | Markel et al. |
| 5,092,846 A * | 3/1992 | Nishijima et al. ..... 604/167.04 |
| 5,092,857 A | 3/1992 | Fleischhacker |
| 5,106,368 A | 4/1992 | Uldall et al. |
| 5,114,408 A | 5/1992 | Fleischhaker et al. |
| 5,149,330 A | 9/1992 | Brightbill |
| 5,156,596 A | 10/1992 | Balbierz et al. |
| 5,158,540 A | 10/1992 | Wijay et al. |
| 5,163,906 A | 11/1992 | Ahmadi |
| 5,207,648 A | 5/1993 | Gross |
| 5,215,527 A | 6/1993 | Beck et al. |
| 5,219,335 A | 6/1993 | Willard et al. |
| 5,221,256 A | 6/1993 | Mahurkar |
| 5,246,016 A | 9/1993 | Lieber et al. |
| 5,250,038 A | 10/1993 | Melker et al. |
| 5,295,962 A | 3/1994 | Crocker et al. |
| 5,328,480 A | 7/1994 | Melker et al. |
| 5,360,414 A | 11/1994 | Yarger |
| 5,364,376 A | 11/1994 | Horzewski et al. |
| 5,364,377 A | 11/1994 | O'Neil |
| 5,376,077 A | 12/1994 | Gomringer |
| 5,378,230 A | 1/1995 | Mahurkar |
| 5,391,152 A | 2/1995 | Patterson |
| 5,403,291 A | 4/1995 | Abrahamson |
| 5,435,308 A | 7/1995 | Gallup et al. |
| 5,451,206 A | 9/1995 | Young |
| 5,456,673 A | 10/1995 | Ziegler et al. |
| 5,464,398 A | 11/1995 | Haindl |
| 5,472,417 A | 12/1995 | Martin et al. |
| 5,472,418 A * | 12/1995 | Palestrant .................... 604/43 |
| 5,486,159 A | 1/1996 | Mahurkar |
| 5,527,292 A | 6/1996 | Adams et al. |
| 5,599,324 A | 2/1997 | McAlister et al. |
| 5,601,603 A | 2/1997 | Illi |
| 5,607,462 A | 3/1997 | Imran |
| 5,613,954 A | 3/1997 | Nelson et al. |
| 5,618,267 A | 4/1997 | Palestrant |
| 5,700,251 A | 12/1997 | Miyauchi et al. |
| 5,718,692 A | 2/1998 | Schon et al. |
| 5,728,064 A | 3/1998 | Burns et al. |
| 5,749,889 A | 5/1998 | Bacich et al. |
| 5,800,384 A | 9/1998 | Russell et al. |
| 5,800,414 A | 9/1998 | Cazal |
| 5,807,311 A | 9/1998 | Palestrant |
| 5,810,776 A | 9/1998 | Bacich et al. |
| 5,827,243 A | 10/1998 | Palestrant |
| 5,879,324 A | 3/1999 | von Hoffmann |
| 6,312,374 B1 | 11/2001 | von Hoffmann |

* cited by examiner

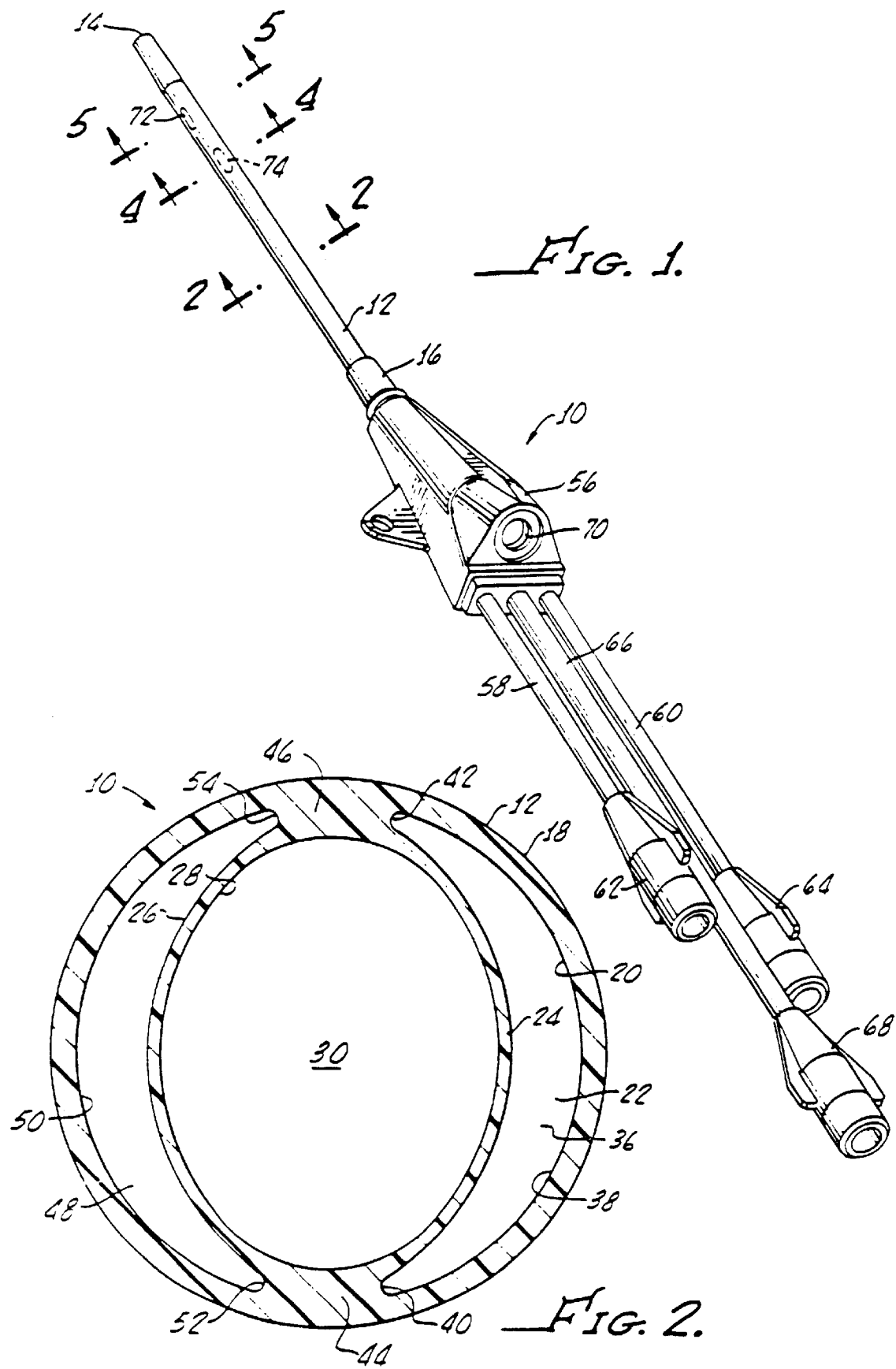

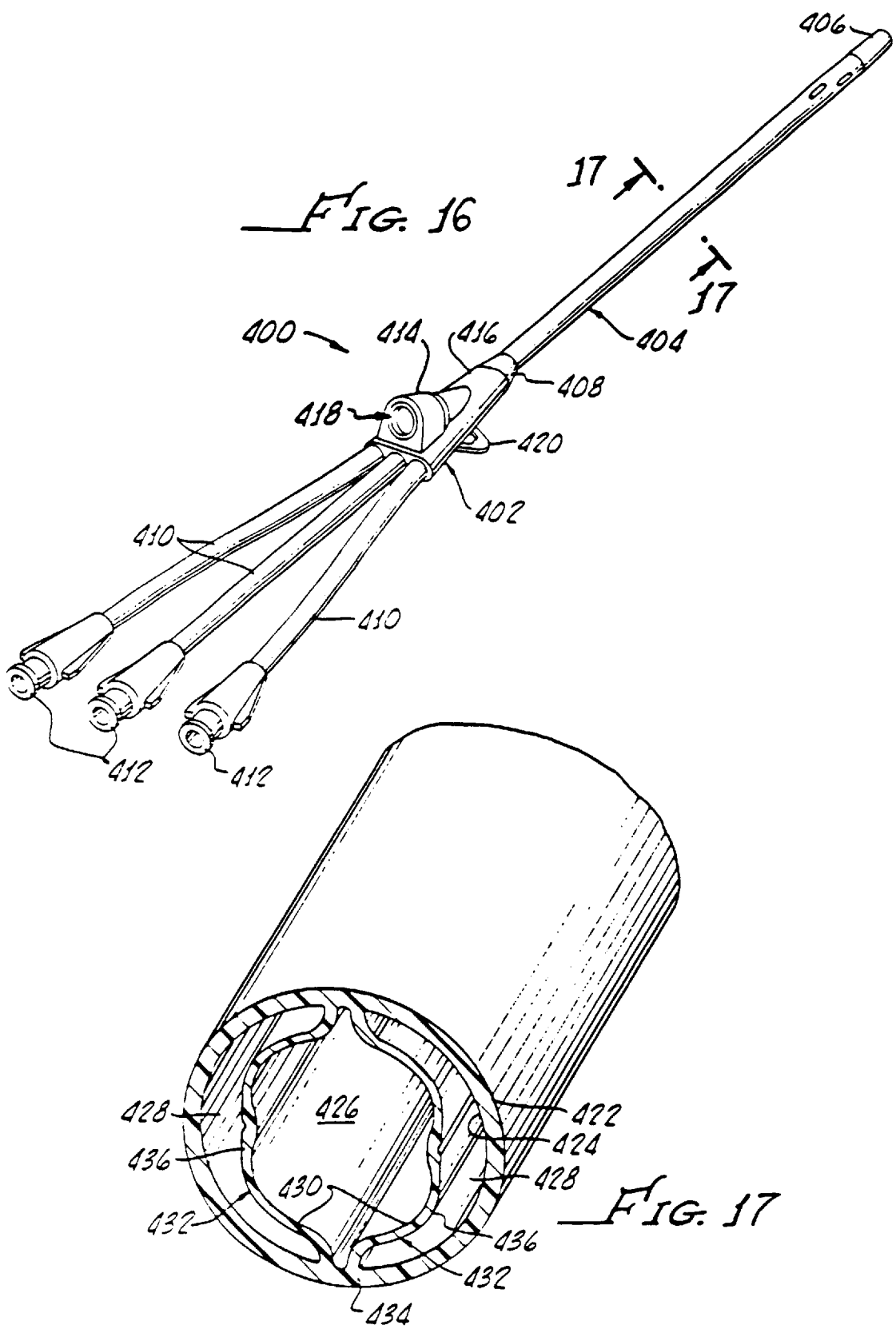

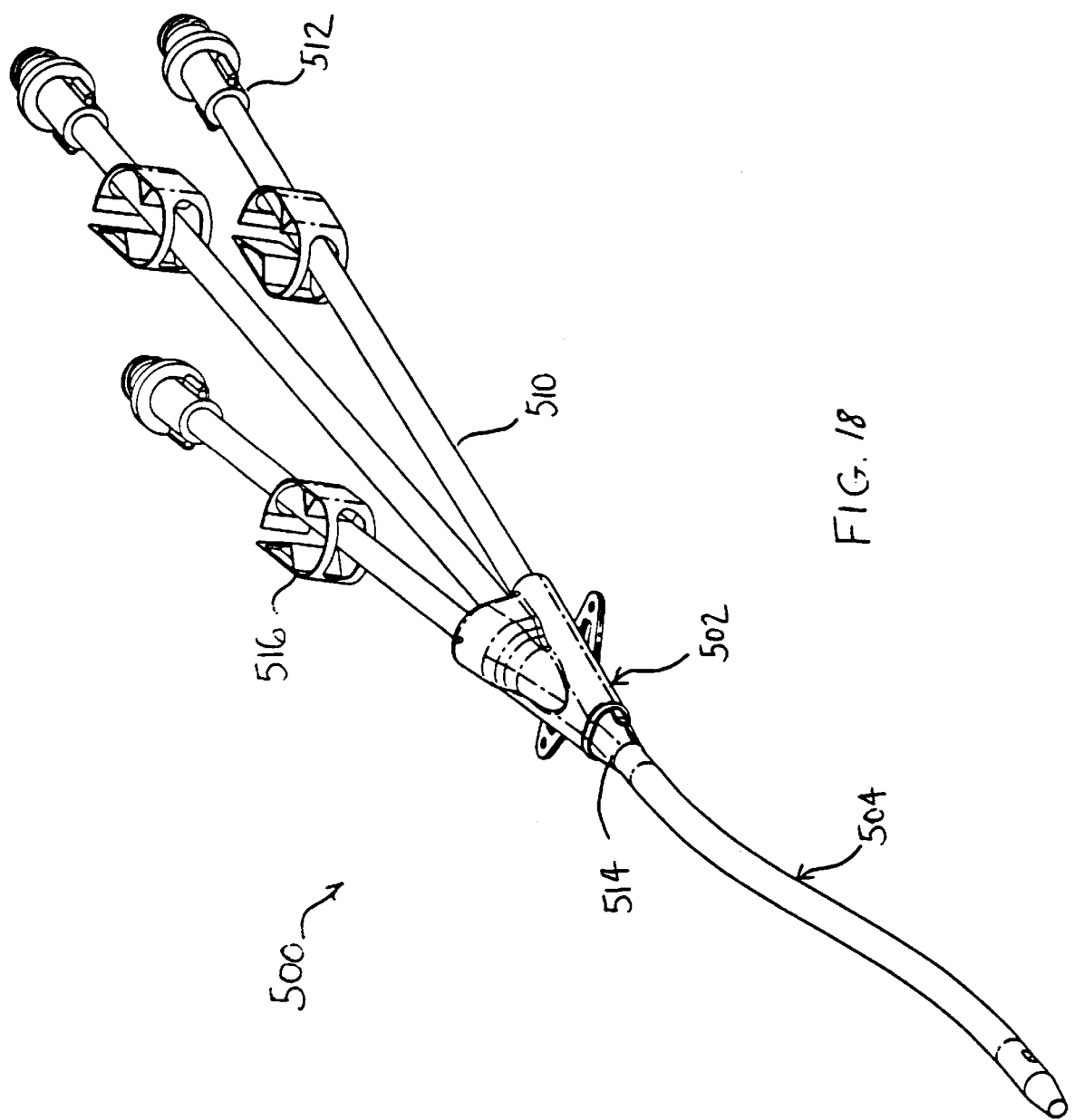

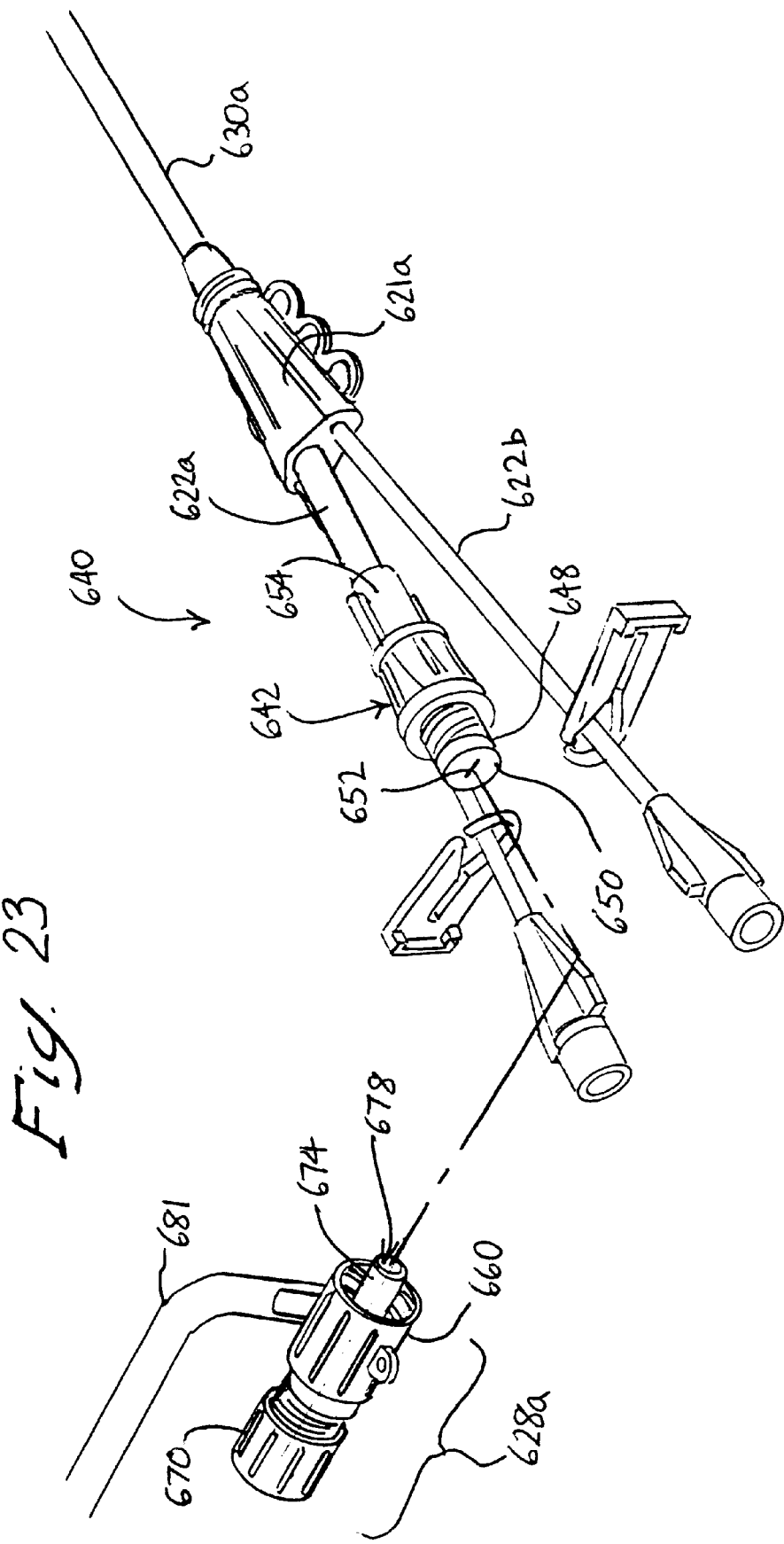

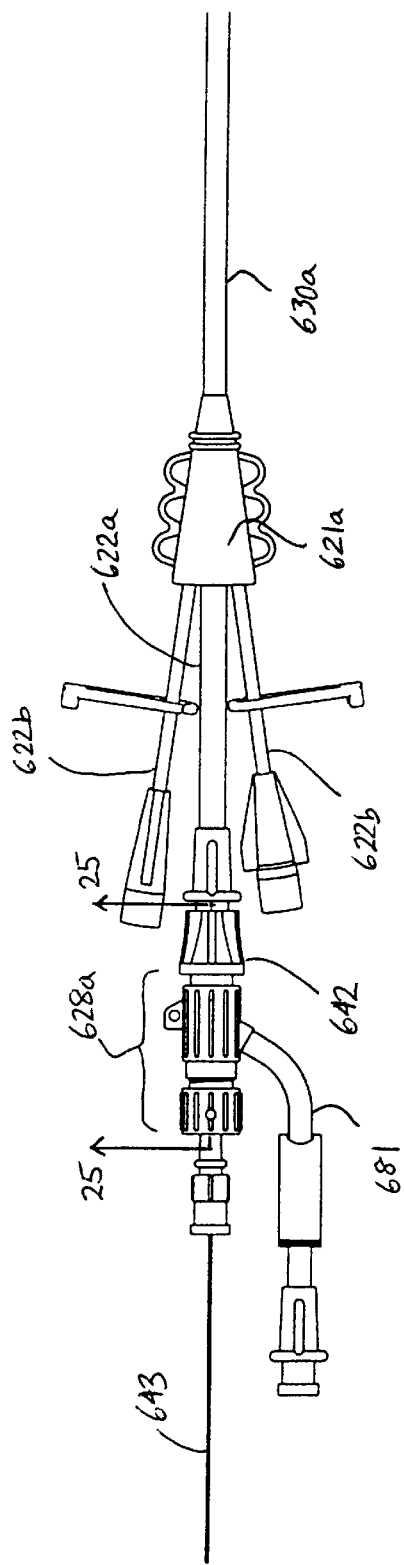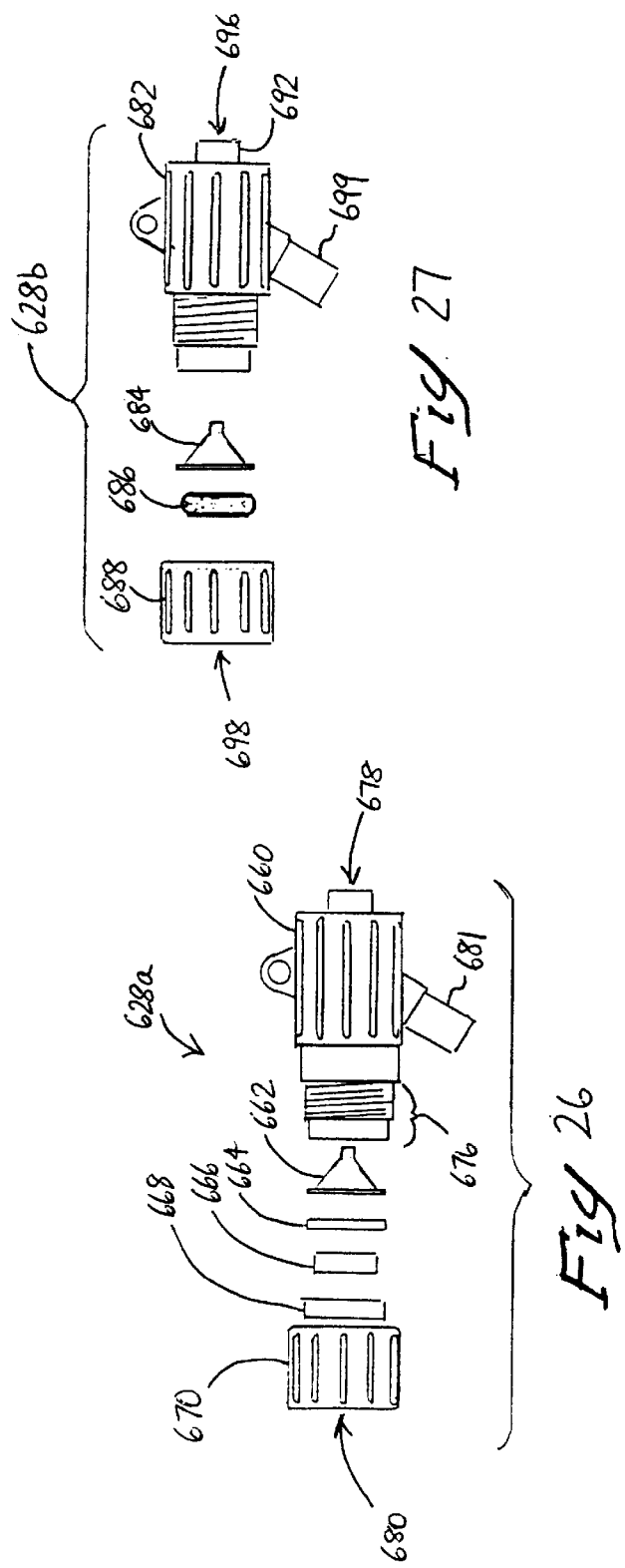

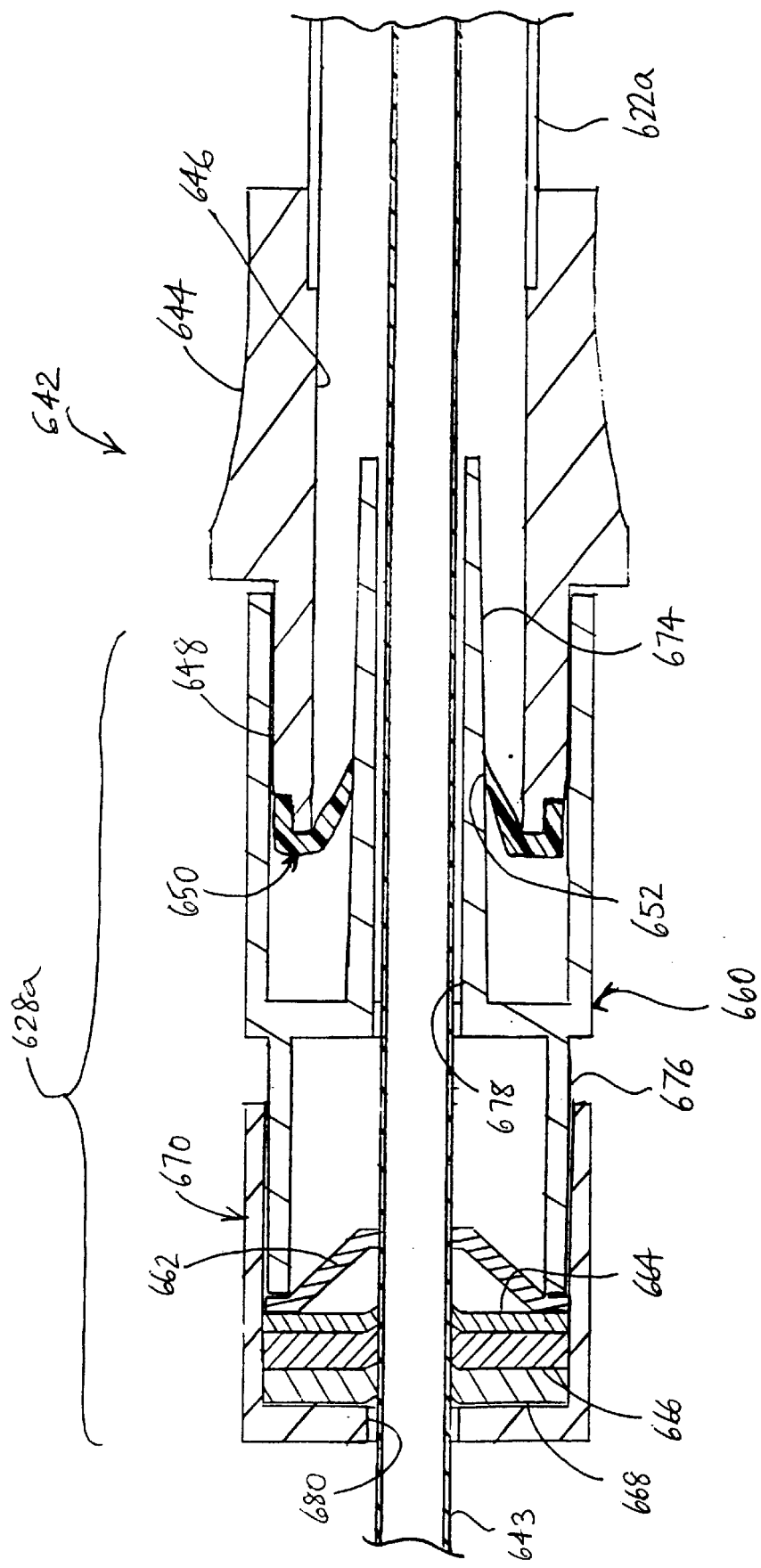

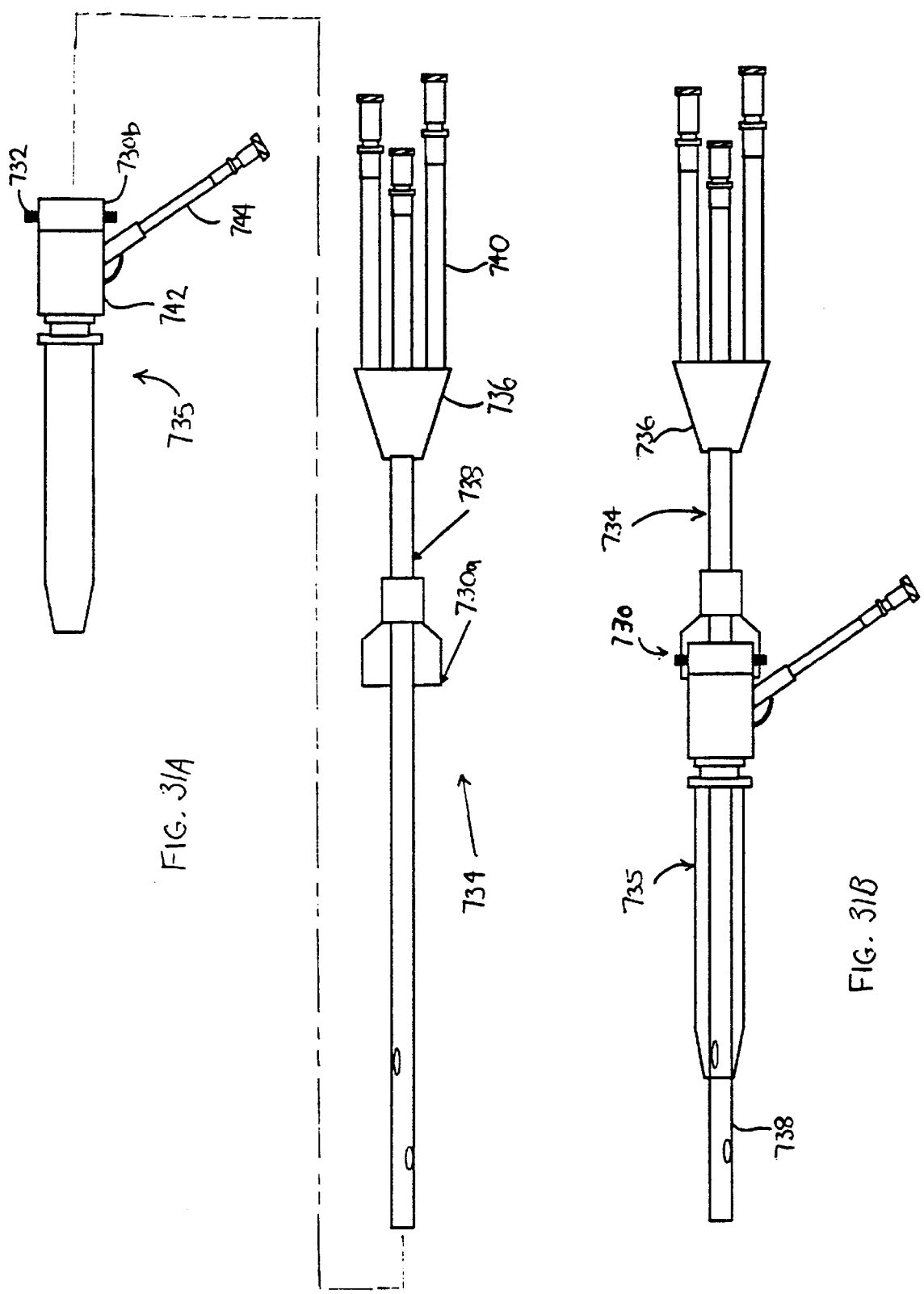

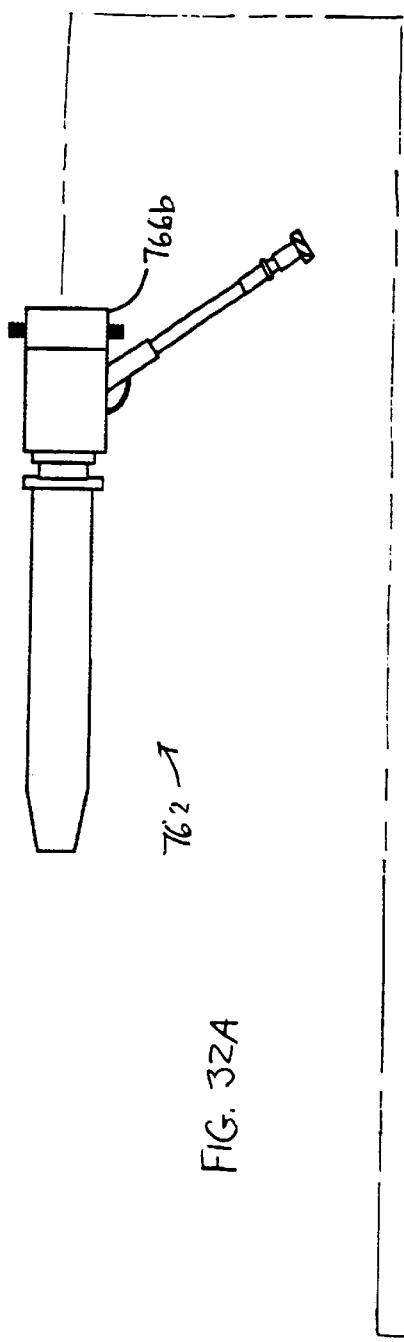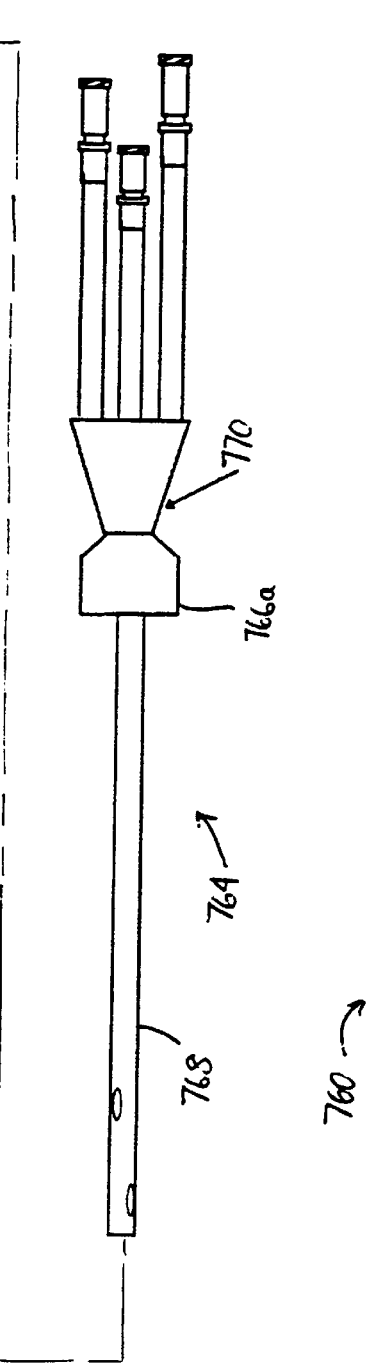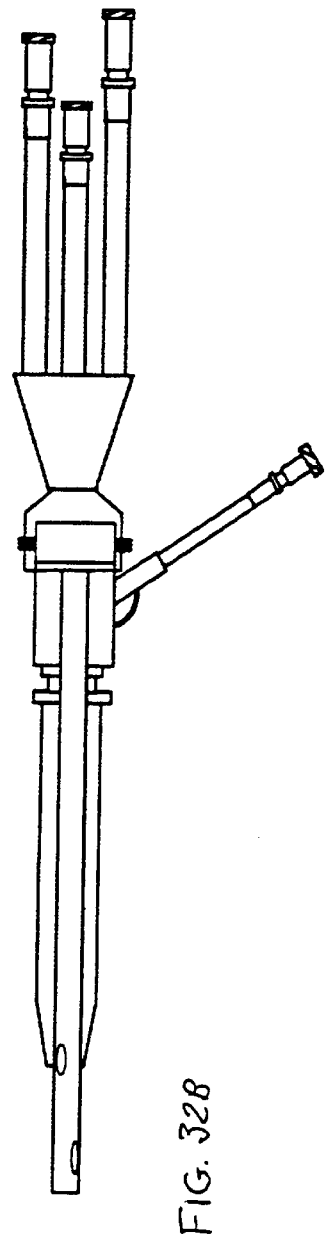
FIG. 32A
FIG. 32B

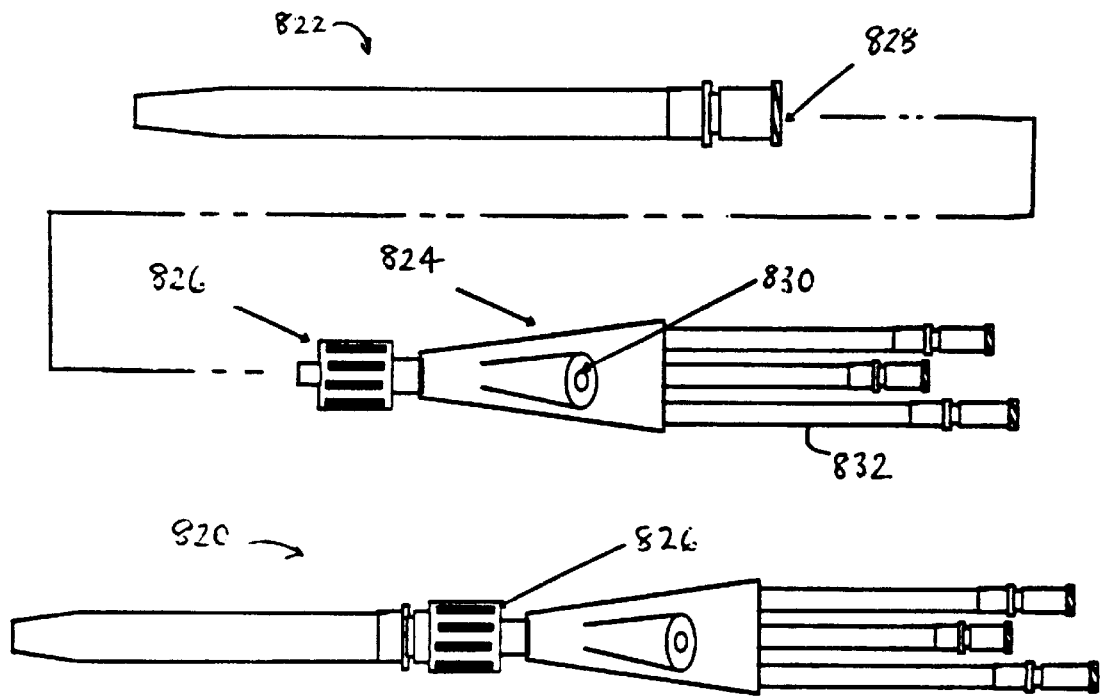
FIG. 34A
FIG. 34B
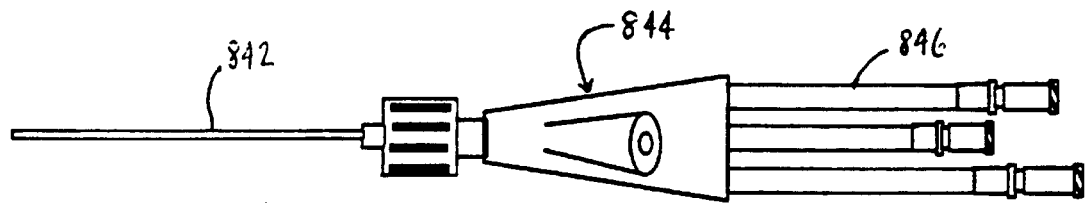
FIG. 35A
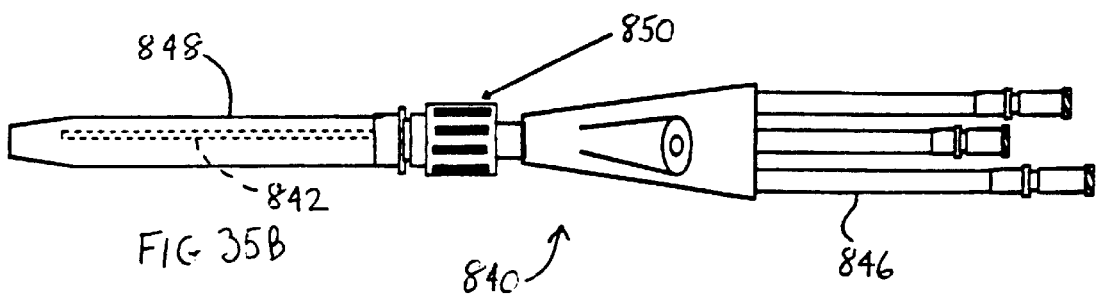
FIG. 35B

VASCULAR ACCESS DEVICES HAVING HEMOSTATIC SAFETY VALVE

BACKGROUND OF THE INVENTION

1. Field of the Invention

The present invention relates generally to medical devices which are used to provide access into the human body and, more particularly, to access devices which provide a single, relatively long-term, entry port into the body. The devices each include a detachable hemostasis valve and a nondetachable safety valve to prevent backflow of bodily fluids upon removal of the hemostasis valve.

2. Description of Related Art

A wide variety of medical devices have been developed in recent years for providing access into the human blood stream. These devices have traditionally been divided into two different groups based on their function and purpose. The first group of devices includes catheters which are designed to introduce therapeutic and/or diagnostic fluids into the blood stream. The second group includes devices commonly referred to as "introducers" which are designed to provide an intermediate term access port into the body through which various medical implements may be passed for therapeutic and/or diagnostic purposes. As a generalization, catheters are longer and more flexible than introducers.

Central venous catheters are relatively long tubular devices which have tapered distal tips which are designed for entry into central veins to provide a dedicated route of fluid infusion into the body. The original venous catheters were single lumen devices which provided the ability to infuse a single liquid into the vein at one time. Multiple lumen catheters have since been developed which allow simultaneous introduction of two or more liquids into the vein. The central venous pressure catheter is a type of common multiple lumen catheter which allows the simultaneous introduction and withdrawal of fluids as well as the capability of monitoring blood pressure and other vital parameters. The portion of the catheter which remains outside of the body has been continually refined and redesigned to provide a low profile which increases comfort and reduces the awkwardness associated with a dedicated tube exiting the body.

Introducers are substantially different from catheters in both design and purpose. An introducer is an access device which is intended to provide a dedicated access port into the body. Catheters, on the other hand, are intended to be used to infuse or withdraw fluids from the body. Introducers typically include a relatively short lumen through which various medical implements, including catheters, can be selectively introduced and removed from the body. An important feature of any introducer is the valve assembly. The valve assembly provides a constant seal between the blood stream and the in vitro environment as medical implements are introduced and withdrawn from the body. The valve assembly is typically located outside of the body at the proximal end of the introducer. As a result, the proximal end of introducers has tended to be relatively bulky.

In addition to a valve assembly, many introducers include a side arm at the proximal end. The side arm is connected to the lumen so that fluids can be introduced into the body simultaneously with the medical device. The introducer lumen is considered to be a "shared" lumen in that the lumen provides a common conduit for both medical implements and fluid pharmaceuticals or diagnostics.

The currently available introducers and other access devices are well-suited for their intended purpose. However, new medical treatments and diagnostic procedures are continually being developed which require more versatile access into the body. For example, organ transplant procedures and cardiac angioplasty require the introduction of complex combinations of medical implements and diagnostic/therapeutic fluids into the body. Many of the presently available access devices are not well-suited for these relatively complex procedures. As a result, multiple access devices are required which must be located at multiple access sites necessitating multiple entry punctures. Accordingly, there is a continuing need to provide improved access devices that have additional capabilities which increase their versatility and usefulness for the increasing variety of invasive treatments and procedures.

SUMMARY OF THE INVENTION

In accordance with the present invention, an improved access device is provided which incorporates a combination of a device lumen valve and a safety valve associated with the device lumen to prevent backflow and leakage of blood from said lumen. In certain embodiments, the present invention is an improvement over existing introducers and other access devices in that multiple lumen access is provided through the introducer in addition to the shared lumen which is used for both medical implements and fluid pharmaceuticals or diagnostics. As an advantage, the improved access device reduces the number of devices required to introduce multiple implements and fluids into the body during complex surgical and diagnostic procedures.

It should be noted that the present invention provides a supplemental safety valve for various vascular access devices, including single or multiple lumen devices. The present disclosure includes a substantial portion of co-pending application Ser. No. 09/329,002, filed Jun. 8, 1999, entitled "MULTIPLE LUMEN ACCESS DEVICE AND METHOD," the disclosure of which is hereby expressly incorporated by reference. This prior application pertains to multiple lumen access devices, broadly defined as having at least one device lumen and at least one auxiliary lumen, typically for infusion. The present supplemental safety valve can be used in combination with many of the embodiments disclosed in the prior application, some of which are included herein as examples. However, the invention can also be used to supplement single lumen access devices, such as standard introducers.

In one exemplary embodiment, the present invention desirably includes a multiple lumen access system for use in providing an entry port into the human body for selectively introducing medical implements therethrough and for providing simultaneous auxiliary access into the body. The system includes a multiple lumen access device comprising an outer tube which has a distal end for introduction into the body and a cross-sectional area. A device lumen through which medical implements may be passed is defined within the cross-sectional area of the outer tube, the device lumen having a distal end and a proximal end. At least one auxiliary lumen is defined within the cross-sectional area and separately from the device lumen, the auxiliary lumen having a distal end and proximal end. Finally, a detachable device lumen valve is associated with the proximal end of the device lumen to provide sealing of the device lumen when medical implements are both present and absent from the device lumen.

A hemostatic safety valve is associated with the device lumen to prevent backflow and leakage of blood from the device lumen when the device lumen valve is purposely or inadvertently detached. Such safety valve may comprise any suitable type of one-way valve or check valve. A particular one-way valve that is useable comprises an elastomeric membrane having a self-sealing opening (e.g. a slit) formed therein. The elastomeric membrane is disposed transversely within the device lumen, or over the proximal end of, the device lumen with its self-sealing opening being biased to a closed or sealed configuration. When no device is inserted through the device lumen, the elastomeric barrier will prevent blood from backflowing in the proximal direction, past the elastomeric barrier, even when the device lumen valve is disconnected or absent. When a device (e.g., another catheter or interventional apparatus) is inserted through the device lumen, it will cause the self-sealing opening of the elastomeric barrier to open sufficiently to allow the device to be inserted therethrough.

A multiple lumen access system according to the present invention may also include ajunction housing having a proximal end and a distal end to which the proximal end of the outer tube connects. The junction housing includes a main channel in fluid communication with the device lumen and at least one auxiliary channel in fluid communication with the at least one auxiliary lumen, the main channel and auxiliary channel(s) diverging from the outer tube to be non-intersecting in the junction housing.

In one embodiment, the main channel and auxiliary channel(s) of the junction housing may be oriented substantially coplanar so that the junction housing is substantially flat, the system further including an extension tube extending from the proximal end of the junction housing and in fluid communication with the main channel wherein the safety valve is connected to the extension tube to therefore be in fluid communication with the main channel. The device lumen valve is then connectable to the safety valve. A side port in the device lumen valve may be provided enabling infusion of fluids to the extension tube and main channel. Furthermore, mating threaded connectors may be included between the device lumen valve and the safety valve enabling easy removal of the device lumen valve. Any appropriate connector, for example a luer connector, may be provided on the device lumen valve, and the system may also include an infusion syringe having a mating luer connector.

The present invention is also directed to a method for introducing medical devices into the body through a single entry port while at all times preventing backflow of fluids through the entry port. In one embodiment, the method includes the steps of providing a vascular access device having a device lumen and a safety valve on the proximal end thereof, introducing the vascular access device into the body with the distal end of the device lumen being positioned within a vasculature of the body; attaching a detachable hemostasis valve to the safety valve to open the safety valve, and inserting a device through the hemostasis valve, open safety valve and device lumen.

The above-described and many other features and attendant advantages of the present invention will become better understood by reference to the following detailed description when taken in conjunction with the accompanying drawings.

BRIEF DESCRIPTION OF THE DRAWINGS

FIG. 1 is a perspective view of an exemplary multiple lumen access device for use with the present invention.

FIG. 2 is a sectional view of FIG. 1 taken in the 2—2 plane of FIG. 1.

FIG. 16 is a perspective view of a further embodiment of a multiple lumen access device for use with the present invention.

FIG. 17 is a perspective sectional view of FIG. 16 taken in the 17—17 plane.

FIGS. 18 and 19 are two perspective views of a multiple lumen access device similar to that shown in FIG. 16.

FIG. 23 is a perspective view of an exemplary multiple lumen access device for use with the present invention having a hemostatic safety valve on the proximal end of the device lumen and a detachable device lumen valve that has been detached from the proximal end of the device lumen.

FIG. 24 is a plan view of the multiple lumen access device of FIG. 23 with the device lumen valve operatively attached to the proximal end of the device lumen, in cooperation with the hemostatic safety valve.

FIG. 25 is a longitudinal sectional view taken along line 25—25 of FIG. 24 of the device lumen valve in cooperation with the hemostatic safety valve.

FIG. 26 is an exploded, side elevational view of one device lumen valve that is useable in the access device of the present invention.

FIG. 27 is an exploded, side elevational view of an alternative device lumen valve that is useable in the access device of the present invention.

FIG. 31A is an exploded view of a multiple lumen access device having an introducer connected to a multi-lumen catheter by an adjustable adapter.

FIG. 31B is an assembled view of the multiple lumen access device of FIG. 31A.

FIG. 32A is an exploded view of a multiple lumen access device having an introducer with infusion port connected to a multi-lumen catheter by an adapter for use with the present invention.

FIG. 32B is an assembled view of the multiple lumen access device of FIG. 32A.

FIG. 34A is an exploded view of a multiple lumen access device having an introducer connected to triple lumen junction housing by a threaded adapter.

FIG. 34B is an assembled view of the multiple lumen access device of FIG. 34A.

FIG. 35A is an exploded view of a multiple lumen access device having an introducer connected to triple lumen junction housing and elongated infusion tube by a threaded adapter.

FIG. 35B is an assembled view of the multiple lumen access device of FIG. 35A.

DESCRIPTION OF THE PREFERRED EMBODIMENTS

Figure 3A:
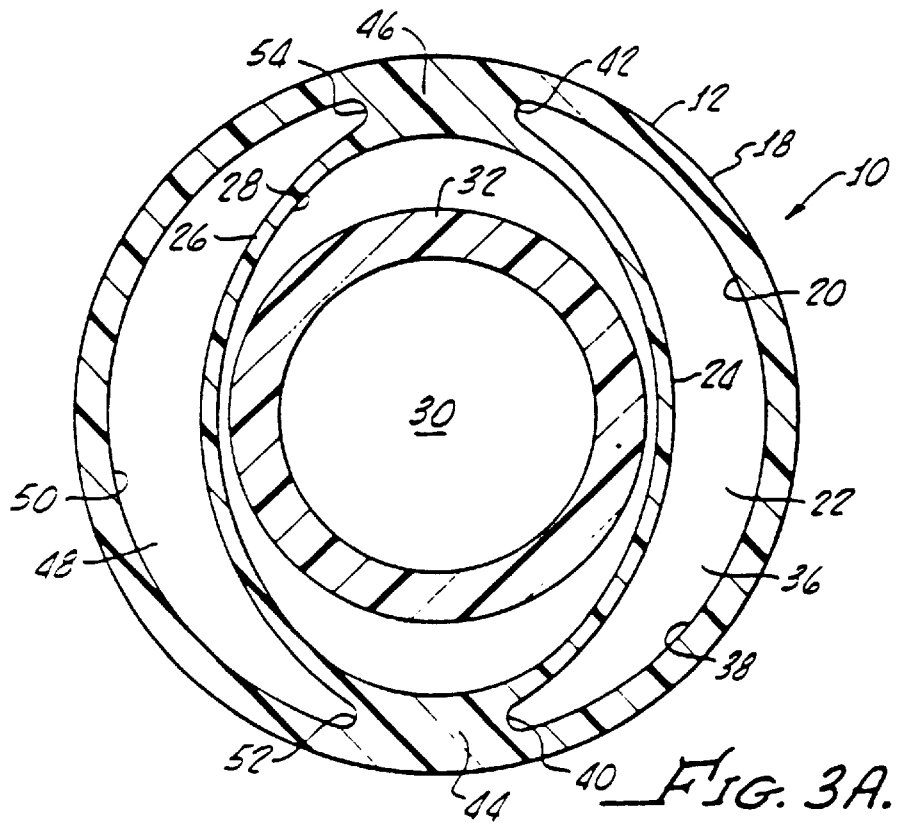
FIG. 3A is a sectional view taken in the same 2—2 plane of FIG. 1 which shows a relatively small diameter medical device located within the device lumen.

An exemplary vascular access device having multiple lumens in accordance with the present invention is shown generally at 10 in FIGS. 1–5. The device 10 includes an outer tube 12 which has a distal end 14 and a proximal end 16. As best shown in FIGS. 2–5, the outer tube 12 has an exterior surface 18 and an interior surface 20. The interior surface 20 defines an access passageway or lumen 22 which has a cross-sectional area that may vary at different locations between the distal 14 and proximal 16 ends of the outer tube 12. Typically, the outer tube 12 may be tapered at the distal end 14, if desired. As a result of the tapering of the outer tube 12, the cross-sectional area will decrease accordingly.

An inner tube 24 is located within the access passageway 22. The inner tube 24 has a distal end and a proximal end which correspond to the distal end 14 and proximal end 16 of the outer tube 12. As illustrated in FIG. 2, the inner tube 24 is formed by a wall surrounding a device lumen 30, the wall having an exterior surface 26 and an interior surface 28. The interior surface 28 defines a device lumen 30 through which medical implements (such as catheters 32 and 34 shown in FIGS. 3A and 3B, respectively) may be inserted into the body. Catheter 34 is also shown in position within the device lumen 30 in FIGS. 4 and 5.

Two auxiliary lumens 36 and 48 are located between the exterior surface 26 of the inner tube 24 and the interior surface 20 of the outer tube 12. The auxiliary lumens 36 and 48 each have a distal end and a proximal end which correspond generally to the distal and proximal ends of the outer tube 12 and inner tube 24. In this particular embodiment, the surfaces which define the auxiliary lumens 36 and 48 correspond to portions of the interior surface of the outer tube and exterior surface of the inner tube. Specifically, auxiliary lumen 36 is defined or bordered by an interior surface 38 which corresponds to the interior surface 20 of the outer tube 12 and the exterior surface 26 of the inner tube 24. Further, the auxiliary lumen 36 is defined by separation surfaces 40 and 42 which are formed by separation barriers 44 and 46, respectively.

A second auxiliary lumen 48 is also formed or defined by the interior surface 20 of the outer tube 12 and the exterior surface 26 of the inner tube 24. Accordingly, the interior surface 50 which defines the second auxiliary lumen 48 corresponds to these surfaces. In addition, the auxiliary lumen 48 is bordered by separation surfaces 52 and 54 formed by separation barriers 44 and 46, respectively.

Referring to FIG. 1, the multiple lumen access device 10 includes a junction housing 56. The junction housing 56 is connected to the proximal end 16 of the access lumen 12. The housing 56 includes infusion tubes 58 and 60 which are connected through the housing 56 to auxiliary lumens 36 and 48, respectively. The infusion tubes 58 and 60 include luer connectors 62 and 64. Other conventional connection devices may be used. A third infusion tube 66 is connected via the housing 56 to the device lumen 30 in order to provide a route for infusion of liquid into the device lumen 30. It should be noted that the infusion tube 66 is not connected to the junction housing 56 at a right angle as is typically done in conventional introducer-type devices. Instead, the infusion tube 66 extends from the housing 56 parallel to the other two infusion tubes 58 and 60. This parallel orientation of the tubes 58, 60 and 66 allows housing 56 to be a low profile body which reduces the bulkiness of the proximal end of the device and increases its wearing comfort. A conventional locking device, such as luer lock 68 is also provided at the proximal end of the infusion tube 66.

The housing 56 includes a valve 70 through which various medical implements are inserted into the device lumen 30. Valve 70 includes a valve or gasket assembly which is designed to provide sealing of the device lumen 30 when medical implements are both present and absent from the device lumen 30. Any of the known gasket arrangements and valve mechanisms used to provide sealing of introducers and related medical implement access devices are suitable. The multiple lumen access device 10 is designed for use in combination with providing access to either the arterial or venous sides of the bloodstream.

Although the device 10, as shown in FIG. 1, includes a non-detachable device lumen valve 70, it also includes infusion tubes 58, 60, and 66 that can be modified to include the safety valve of the present invention, as described below with respect to FIGS. 23–27. Therefore, the combination of various aspects of the device 10 and the safety valve assembly of the present invention is within the scope of the present invention.

An opening 72 (see FIG. 1 and FIG. 5) is provided towards the distal end of outer tube 12. The opening 72 is provided to allow exit of fluid from auxiliary lumen 48 which has been introduced through infusion tube 58. Likewise, an opening 74 (shown in phantom in FIG. 1 and also shown in FIG. 4) is provided for allowing the fluid introduced through infusion tube 60 to exit auxiliary lumen 36 at the proximal end of the outer tube 12.

Figure 4:
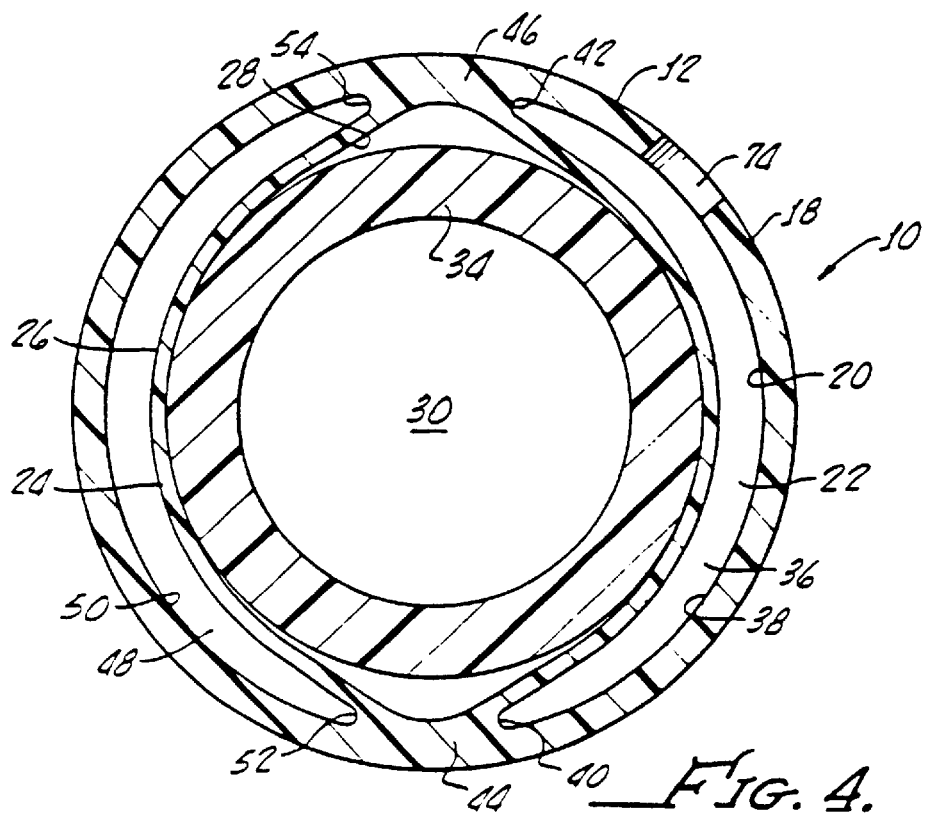
FIG. 4 is a sectional view of FIG. 1 taken in the 44 plane.
Figure 5:
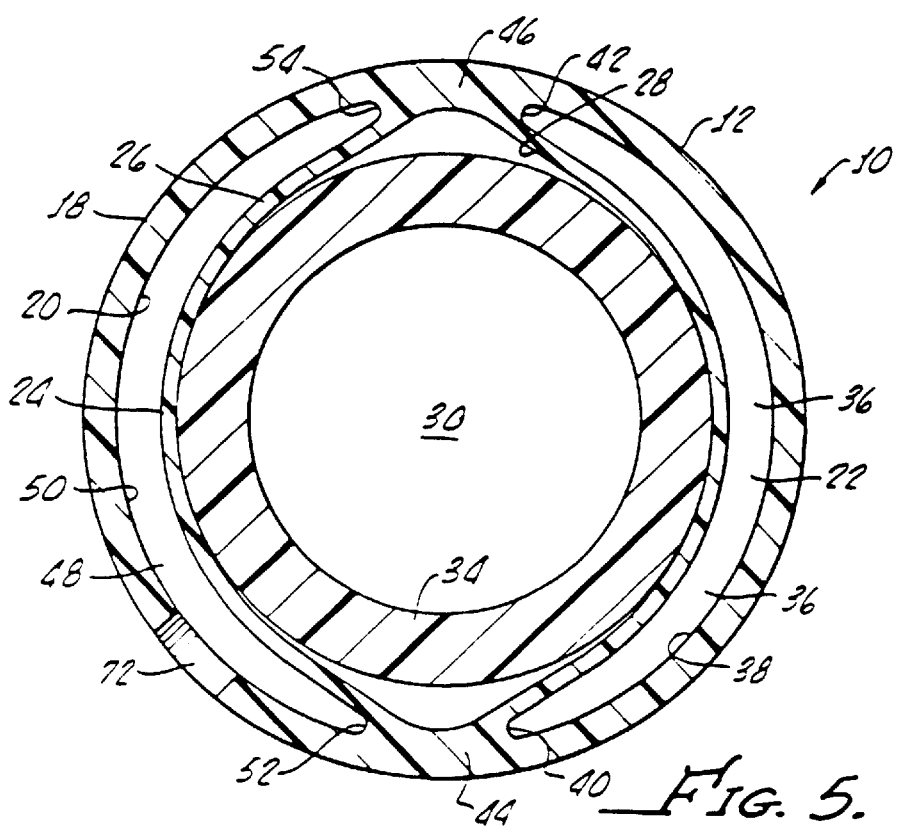
FIG. 5 is a sectional view of FIG. 1 taken in the 5—5 plane.

As illustrated in FIGS. 1, 4 and 5, the openings 72 and 74 are preferably sized to avoid restricting fluid flow through the respective auxiliary lumens. Therefore, it is preferred that the openings 72 and 74 are each sized sufficiently large to be equal or greater than the maximum distended/expanded cross-sectional area of the corresponding auxiliary lumens 36 and 48. Of course, this same principle applies with regard to any number of auxiliary lumens each having a variable cross-section. When either auxiliary lumen 36, 48 is under pressure and no device is present in the device lumen 30, the auxiliary lumen cross-section increases in diameter. In one preferred embodiment, the auxiliary lumen increases, for example, from approximately 15 gauge to about 12 gauge, while in another embodiment the auxiliary lumen increases from approximately 18 gauge to about 14 gauge. Therefore, the openings 72 and 74 are each sized to be equivalent to or greater than 12 gauge or 14 gauge, respectively, to avoid restricting fluid flow through the respective auxiliary lumen. When other cross-section diameters of the auxiliary lumens are used, the size of the openings, such as 72 and 74, are preferably sized accordingly.

Figure 3B:
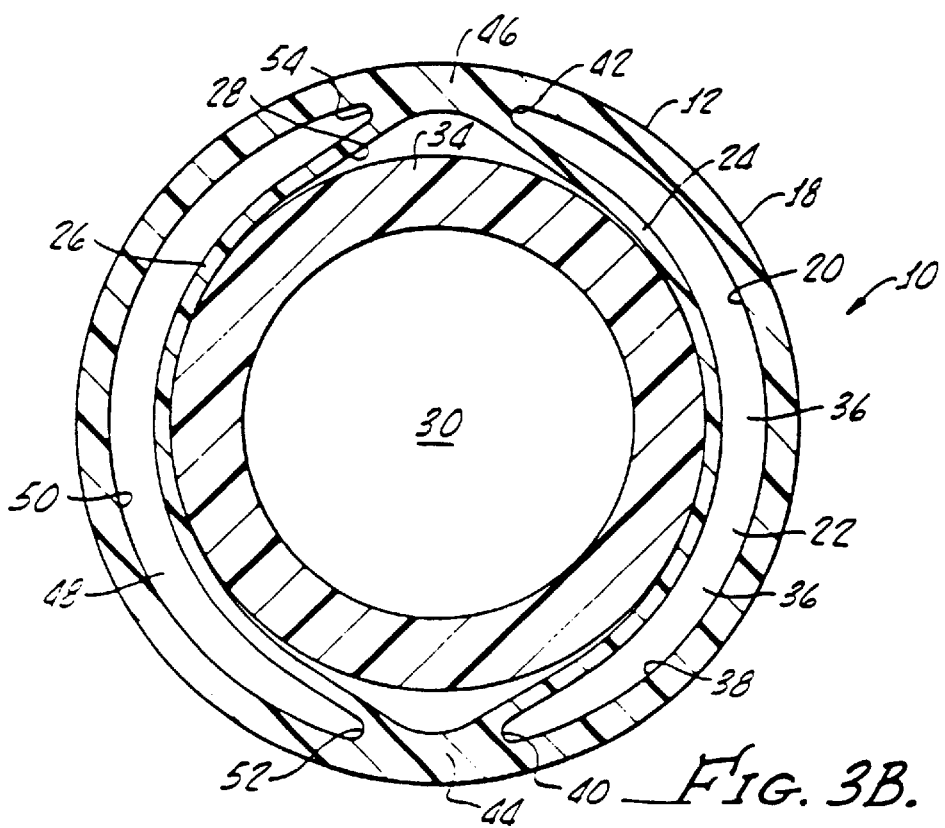
FIG. 3B is a sectional view taken in the same 2—2 plane of FIG. 1 showing a relatively large diameter medical implement located within the device lumen.

In this exemplary embodiment, the inner tube 24 must be sufficiently flexible to be stretchable between a relaxed position as shown in FIG. 3A and various expanded positions as exemplified in FIG. 3B. In FIG. 3A, a catheter 32 having a diameter of 1.3 millimeter (4 French) is shown inserted within the device lumen 30. The inner tube 24 is in a relaxed position where the cross-sectional area of the device lumen 30 is approximately 2 square millimeters. The relaxed cross-sectional area of the device lumen 30 will preferably range from 1 to 3 square millimeters. Larger diameters are possible, if desired. It is preferred, but not required, that inner tube 24 have a circular or elliptical cross-section.

As shown in FIG. 3B, a larger diameter catheter 34 has been inserted into the device lumen 30. The inner wall 24 is made from sufficiently resilient material and is sufficiently sized so that it can expand to the diameter shown which is approximately 3 millimeter (9 French). The maximum diameters to which the inner tube 24 can be expanded is limited by the diameter of the outer tube 12. The inner tube 24 may be flexed inward, if desired, by applying fluid pressure through one or both auxiliary lumens 36 and 48. Typically, the cross-sectional area of the device lumen 30 when the inner tube 24 is in its maximum expanded state will range from 5 to 9 square millimeters. Larger diameters are possible, if desired. Preferably, the inner tube 24 will be sufficiently flexible so that it can be expanded completely outward against the interior surface 20 of the outer tube 12. In the fully expanded state, the auxiliary lumens 36 and 48 will have substantially reduced cross-sectional areas. However, it is preferred that the auxiliary lumens 36 and 48 not be entirely closed. It is desirable to leave some opening through these two auxiliary lumens 36 and 48 at all times to allow flushing fluids to be passed through the lumens in order to prevent the formation of blood clots or other problems associated with a completely collapsed lumen.

Preferably, the inner tube 24 is sufficiently flexible to be stretched to expanded positions wherein the cross-sectional area of the device lumen 30 in the expanded state is up to 85 percent of the cross-sectional area of the access lumen 22. This allows for continual auxiliary fluid introduction through auxiliary lumens 36 and 48. Further, it is preferred that in the relaxed position as shown in FIG. 3, that the device lumen 30 have a cross-sectional area which is not less than 35 percent of the cross-sectional area of the access lumen 22.

The inner tube 24 is preferably connected to the outer tube 12 at separation barriers 44 and 46 in order to divide the access lumen 22 into a three-chamber lumen, i.e. the central device lumen 30 and two auxiliary lumens 36 and 48. In order to achieve the desired flexibility of the device lumen 30, it is preferred that a relatively elastic material be utilized. Suitable elastic materials include, but are not limited to, polyvinylchloride, polyurethane, polyethylene, nylon, silicone, fluoropolymers and polypropylene. Further, in order to achieve the desired variation in lumen cross-sectional areas, the thickness and durometer of the inner tube walls 24 must be carefully matched to the particular material being utilized. For less flexible materials, the wall thicknesses must be correspondingly reduced in order to achieve the desired flexibility limits. The inner tube 24 should be sufficiently flexible so that it can be expanded to diameters which are at least as large as the outer tube 12.

Figures 6, 7, 8:
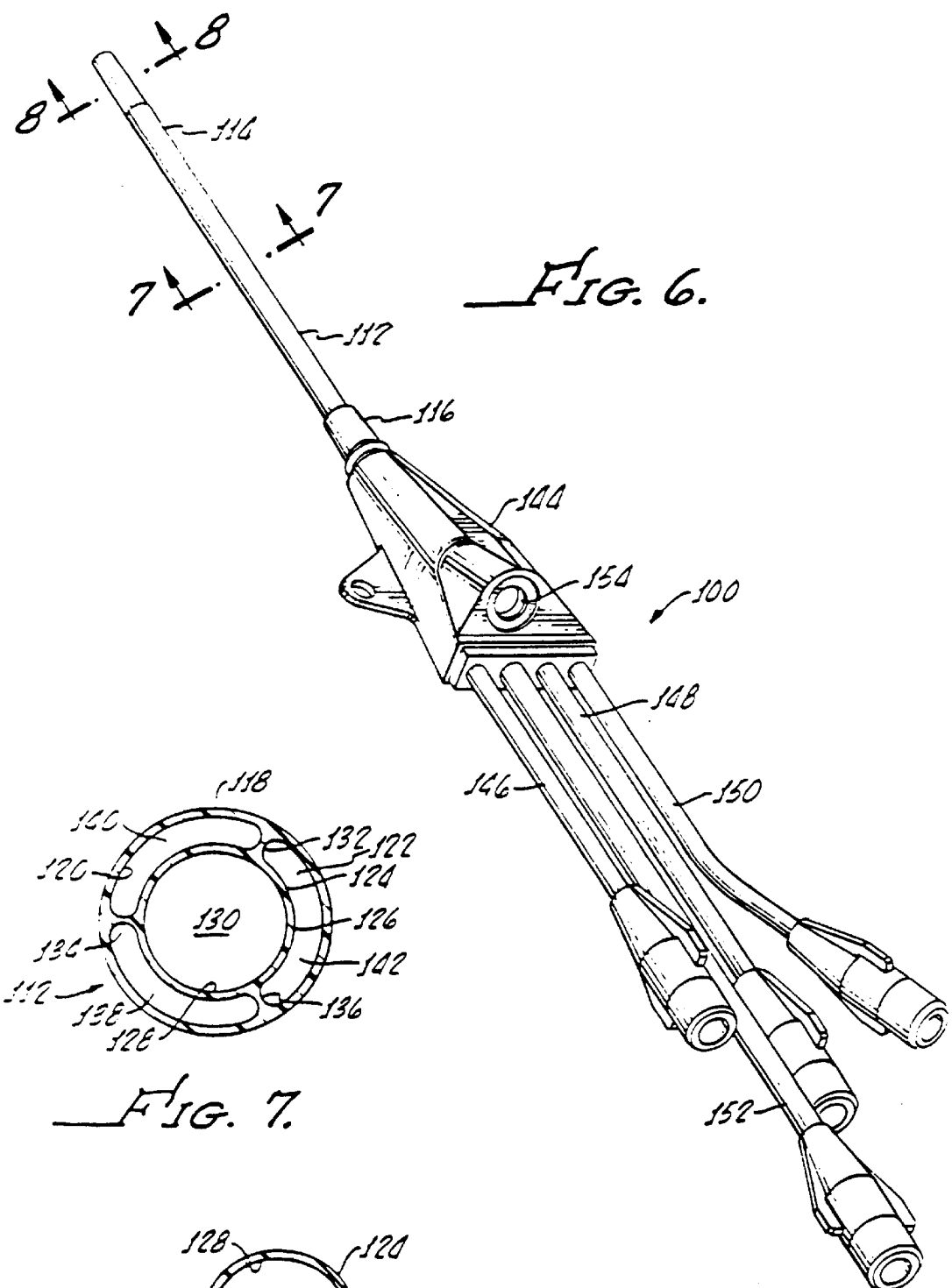
FIG. 6 is a perspective view of another exemplary embodiment for use with the present invention.
FIG. 7 is a sectional view of FIG. 6 taken in the 7—7 plane.
FIG. 8 is a sectional view of FIG. 6 taken in the 8—8 plane.

Another exemplary embodiment of the access device for use with the present invention is shown generally at 100 in FIG. 6. The access device 100 is similar to the previous preferred embodiments in that it includes an outer tube 112 having a distal end 114 and a proximal end 116. As best shown in FIGS. 7 and 8, the outer tube 112 has an exterior surface 118 and an interior surface 120. The interior surface defines an access passageway 122 in which an inner tube 124 is located. The inner tube 124 includes an exterior surface 126 and an interior surface 128. The interior surface 128 of the inner tube 124 defines a device lumen 130 through which medical implements, such as a catheter, may be inserted. The access device 100 includes three separation barriers 132, 134 and 136 which, in combination with the interior surface of the outer tube 120 and exterior surface of the inner tube 126, form three auxiliary lumens 138, 140 and 142. The multiple lumen access device 100 includes the same type of junction housing 144 which was described in the previously-described embodiment (FIGS. 1–5), except that an additional infusion lumen is included to provide infusion of liquid into the additional auxiliary lumen. As shown in FIG. 6, infusion lumens 146, 148 and 150 are connected via junction housing 144 to auxiliary lumens 138, 140 and 142, respectively. A primary infusion lumen 152 is also provided for introducing fluids into the device lumen 130. Again, an access port 154 is provided with the appropriate gaskets and/or valving mechanism to allow introduction of catheters and other medical devices into the device lumen 130.

The inner tube 124 in this exemplary embodiment may or may not be made from flexible material. The inclusion of three separation barriers in this particular embodiment reduces the ability for flexible expansion and contraction of the inner tube 124. However, it is preferred that the material used to form the device lumen 124 and the separation barriers be more flexible than the exterior outer tube 112 in order to allow variations in the cross-sectional areas of the auxiliary lumens. Otherwise, the same materials and fabrication techniques which are used to fabricate the prior embodiments are also suitable for use in making the multiple lumen access device 100.

Figure 9:
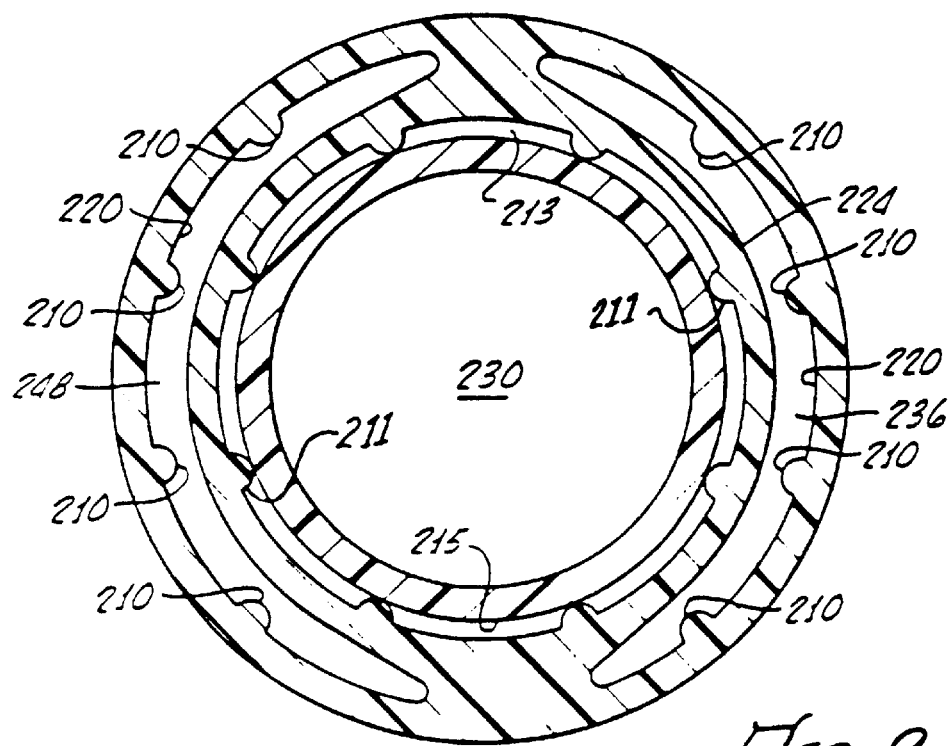
FIG. 9 is a sectional view of an exemplary flexible inner wall showing the location of spacing ribs.

In the embodiment shown in FIG. 9, spacer ribs 210 are provided on the interior surface 220 of the outer tube 212 to prevent the inner tube 224 from being expanded to a position which closes the auxiliary lumens 236 and 248. Spacer ribs 211 may also be provided to insure that a passageway 213 is maintained around a device 215 when it is located within device lumen 230. The ribs 210 are preferably located longitudinally along the entire length of the outer tube 212 where the inner tube 224 is also present. The particular cross-sectional shape of the spacer ribs 210 is not particularly important so long as they are relatively blunt and do not damage the inner tube 224 during contact therewith. The number and relative positioning of the spacer must be chosen to insure that complete closure of the auxiliary lumens 236 and 248 does not occur. For inner tubes 224 which are relatively flexible, the number and size of ribs may have to be increased. The ribs 210 shown in FIG. 9 are an example of a preferred configuration. The number, shape, size and position of the ribs 210 may be varied as required in order to prevent closure of the auxiliary lumens 236 and 248 as discussed above.

Although more than two auxiliary lumens may be included into the multiple lumen access device, it is preferred that two lumens be utilized. The use of two lumens is a preferred design for allowing uniform expansion of the inner tube 24 between the relaxed state as shown in FIG. 3A and an expanded state as shown in FIG. 3B.

Figure 10:
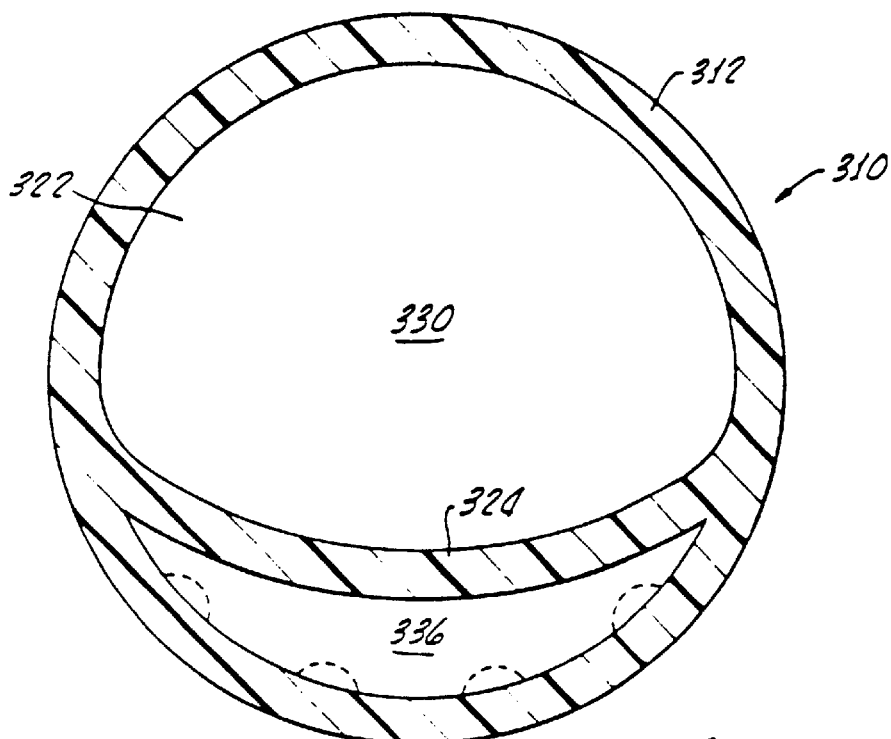
FIG. 10 is a sectional view of an exemplary multiple lumen access device having a single auxiliary lumen.

Access devices which include one auxiliary lumen are also possible. The cross-section of an exemplary access lumen is shown at 310 in FIG. 10. The access lumen 310 includes an outer tube 312 which defines an access lumen 322. The access lumen 322 is divided into a device lumen 330 and an auxiliary lumen 336 by an inner flexible wall 324. The inner surface of the outer wall 312 preferably includes spacer ribs (shown in phantom at 350) to prevent closure of the auxiliary lumen 336. The inner wall 324 is made from the same types of flexible materials as described previously for the inner tubes used in the multiple auxiliary lumen embodiments. This particular embodiment is well-suited for use in those situations where a relatively large device lumen is required in favor of the advantages provided by multiple auxiliary lumens.

The outer wall 12 is preferably made from any of the well-known polymer materials used in fabricating introducers and other access devices. Exemplary materials include polyurethane, polyethylene, polypropylene, nylon, polyester, polyether/ester copolymers, silicone based polymers, metalocene catalyzed polyolefins or ethylene vinyl acetate and synthetic rubbers. Preferably, the material used and wall thicknesses for the outer wall 12 are such that the outer wall 12 is a relatively stiff tube in relation to the inner tube 24. Further, the material used for the outer wall 12 should be compatible for molding purposes with the material used to form the inner wall 24. It is preferred that the outer wall 12 and inner wall 24 be extruded together, as will be more fully described below. The outer wall 12 and inner wall 26 may be made from the same material or different materials. The inner wall 26 is preferably made from softer versions of the various polymers listed above. When using different materials, the materials must be compatible for bonding or fusing together.

Other fabrication techniques for connecting the inner and outer tubes are possible provided that the connection between the two lumens at the separation barriers 44 and 46 extends the entire length of the two lumens and provides a solid integral connection between the lumens. For example, radio frequency (RF) welding of the tubes is another possible fabrication procedure which may be used to make the access lumen in accordance with the present invention. If desired, the entire triple lumen can be extruded as a single integral multiple lumen structure.

During use, the exemplary access device 10 allows introduction of medical implements into the device lumen while at the same time allowing infusion of fluid through tube 66 also into device lumen, as well as allowing infusion through tubes 58 and 60 into auxiliary lumens 48 and 36, respectively. Since, as discussed above, the outer tube 12 is relatively inflexible in the radial direction (though overall longitudinally flexible), the total available cross-sectional area for insertion of medical implements and flow of fluids is limited for a given access device. However, the flexibility of the device lumen allows the doctor or other medical professional to selectively and fully utilize the total available cross-sectional area.

In FIG. 3A, a relatively small catheter 32 is shown inserted within the device lumen 30. In this configuration, fluids may be infused/removed through the unused area of the device lumen 30 as well as the two auxiliary lumens 36 and 48. It should be noted that the preferred design inherently centers the catheter or medical implement 32 so that the auxiliary lumens 36 and 48 have approximately equal cross-sectional areas. However, it should be noted that the application of differential pressure to the infusion tubes 58 and 60 can be used to selectively increase or decrease the relative cross sectional areas available for infusion of fluids through the auxiliary lumens. For example, the size of auxiliary lumen 36 can be increased relative to the cross-sectional size of auxiliary lumen 48 by introducing infusion of liquid through tube 58 at a pressure which is relatively higher than that of tube 60. The double auxiliary lumen design of this exemplary embodiment is especially well suited for providing such differential fluid flows when desired.

Figure 11A:
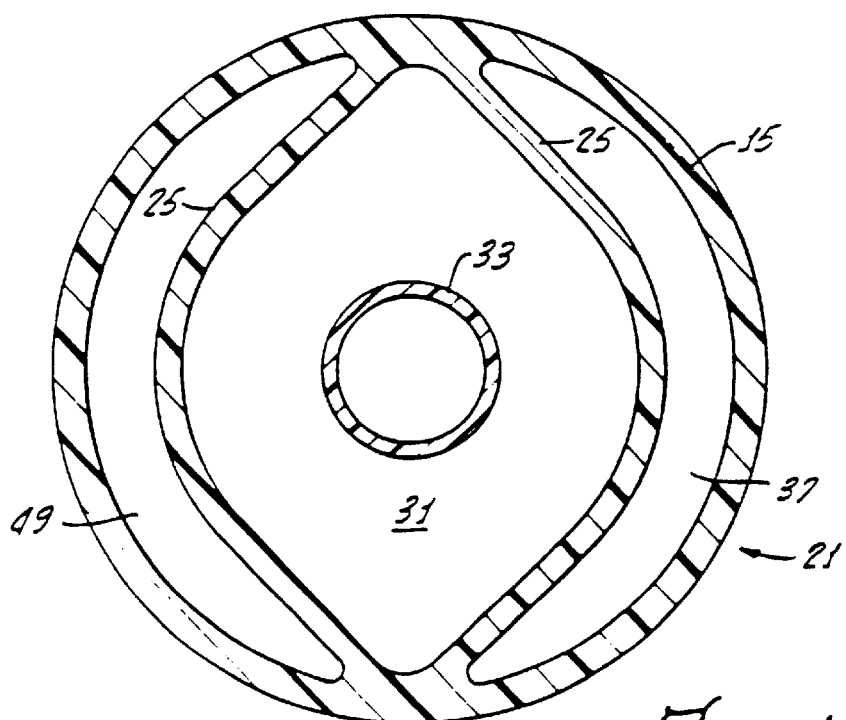
FIGS. 11 A–C are sectional views of an exemplary multiple lumen access device showing a relatively small diameter medical implement located in a central device lumen and the inner walls in relaxed conditions (11A), partially collapsed about the implement due to pressurization of side auxiliary lumens (11B), and substantially completely collapsed about the implement (11C).
Figure 11B:
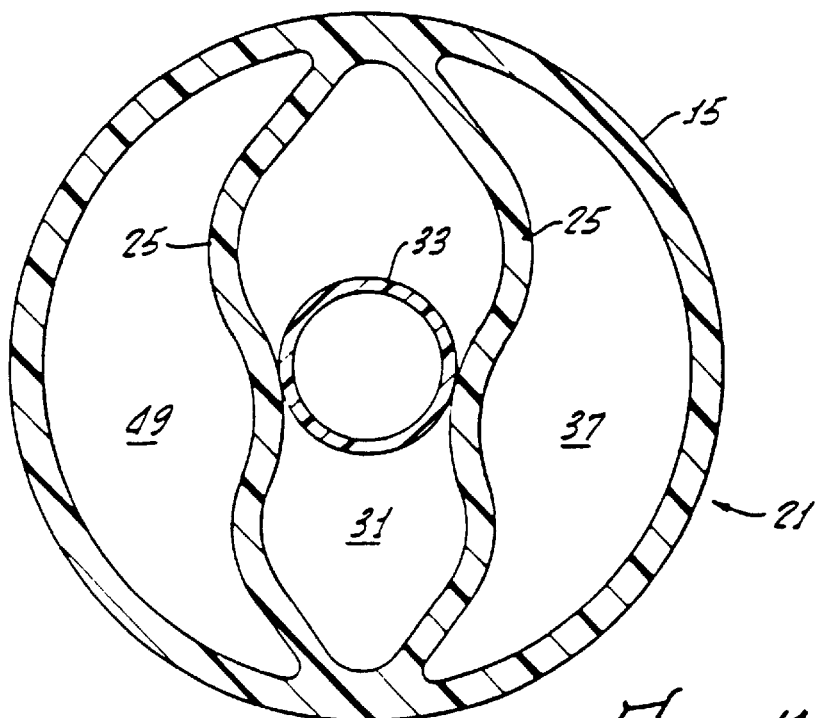
Figure 11C:
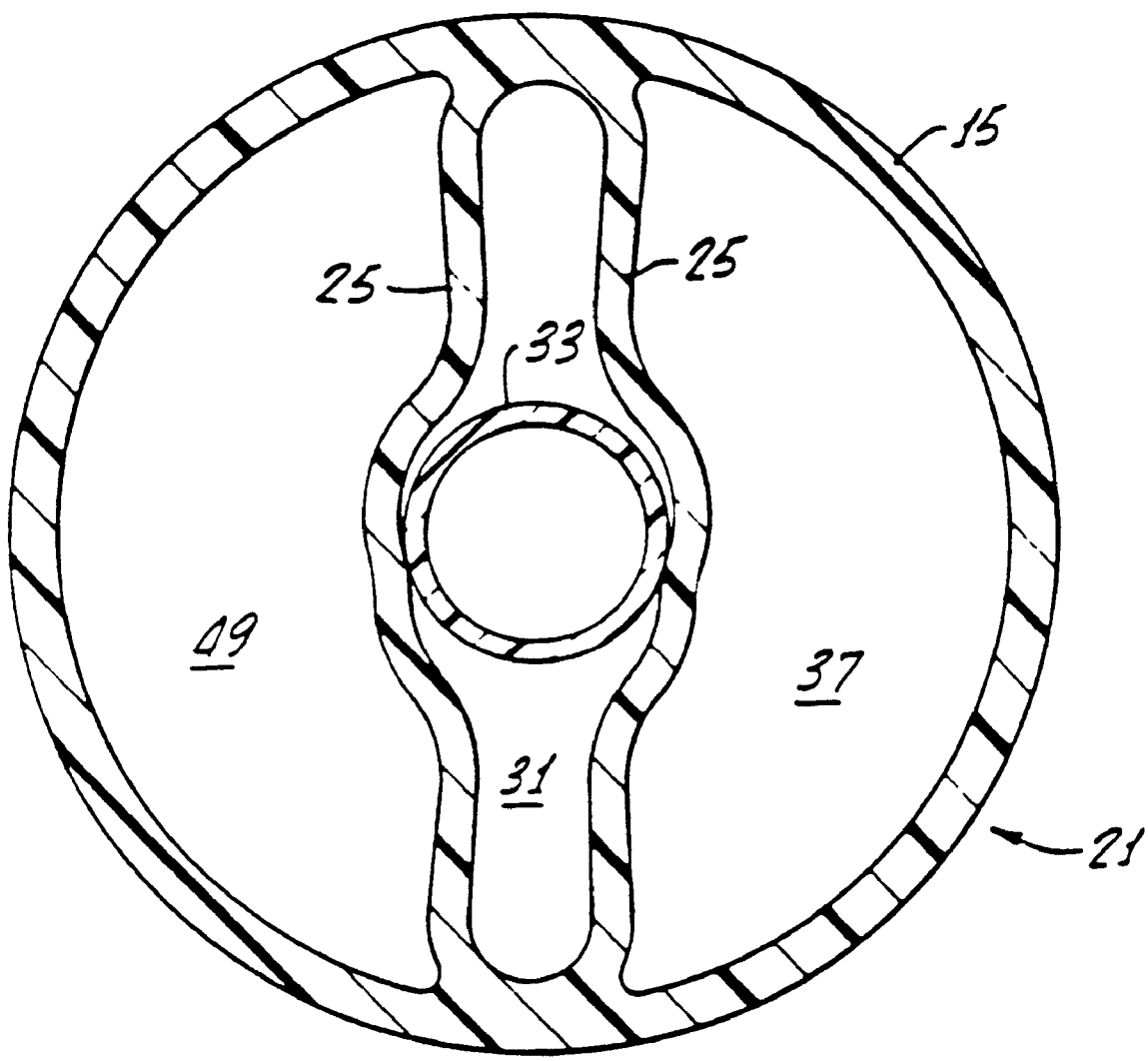

An exemplary embodiment which further demonstrates the flexibility of the described access devices is demonstrated in FIGS. 11A–11C. In FIG. 11A, an exemplary access device 21 is shown in which a relatively small catheter 33 is located within the device lumen 31. In this configuration, fluids may be infused/removed through the unused area of device lumen 31 as well as the two auxiliary lumens 37 and 49. As shown in FIG. 11A, the inner flexible walls 25 is in a relaxed position. In this position, the inner wall 25 is relatively close to the outer wall 15. When desired, the size of the auxiliary lumens 37 and 49 can be increased substantially by increasing the pressure of liquids being passed therethrough. The result, as shown in FIG. 11B, is the partial collapsing of the inner tube or inner walls 25 about the catheter 33. In the partially contracted or collapsed position as shown in FIG. 11B, the inner walls 25 are not stretched. Instead, their configuration changes as shown in FIG. 11B to accommodate the change in relative sizes of the auxiliary lumens and device lumen. As shown in FIG. 11C, the size of auxiliary lumens 37 and 49 are increased even further to a point where the fluid flow through the two auxiliary lumens is maximized. In this condition, stretching of the contracted flexible walls 25 may occur. As is apparent from FIGS. 11A–11C, it is possible to provide a wide variance in fluid flows through the auxiliary lumens and device lumen depending upon differential pressures applied through the various lumens.

Figure 13:
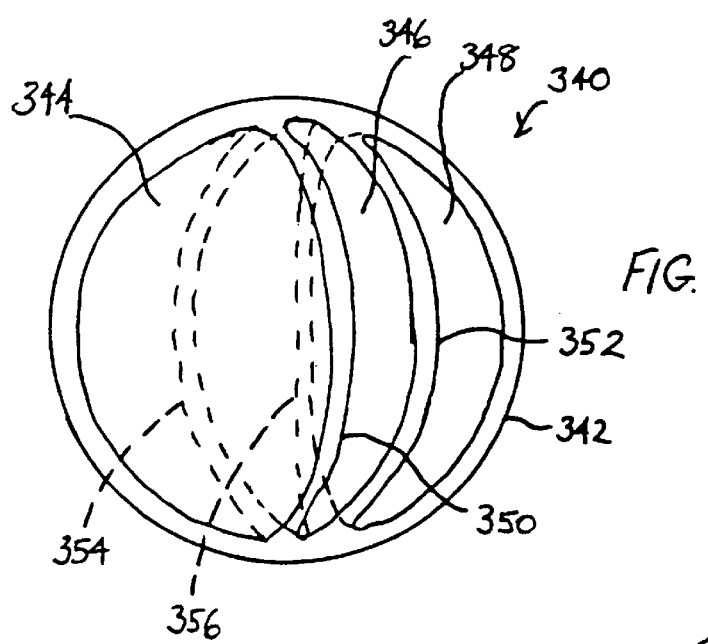
FIG. 13 is a sectional view of an alternative multi-lumen sheath for use in the present invention having a device lumen on one side and two side-by-side auxiliary lumens.

FIG. 13 illustrates an alternative cross-section of a sheath portion 340 for the multiple lumen access device for use with the present invention in which the device lumen is not between two auxiliary lumens. The sheath portion of the devices of the present invention comprise the portion that is distally disposed with respect to the junction housing, defines multiple lumens therein, and is substantially inserted into the patient's vasculature. In FIG. 13, the sheath portion 340 comprises an outer tube 342 defining within, and, in series from left to right, a device lumen 344, a first auxiliary lumen 346, and a second auxiliary lumen 348. A first flexible wall 350 separates the device lumen 344 from the first auxiliary lumen 346, while a second wall 352, that can be flexible or relatively rigid, separates the first and second auxiliary lumens 346, 348. The first flexible wall 350 can move from its position shown in solid line to the dashed-line position shown at 354 as the pressure difference across the wall increases in favor of the first auxiliary lumen 346. Likewise, the second flexible wall 352, if flexible, can move from its position shown in solid line to the dashed-line position shown at 356 as the pressure difference across the wall increases in favor of the second auxiliary lumen 348.

Figure 14:
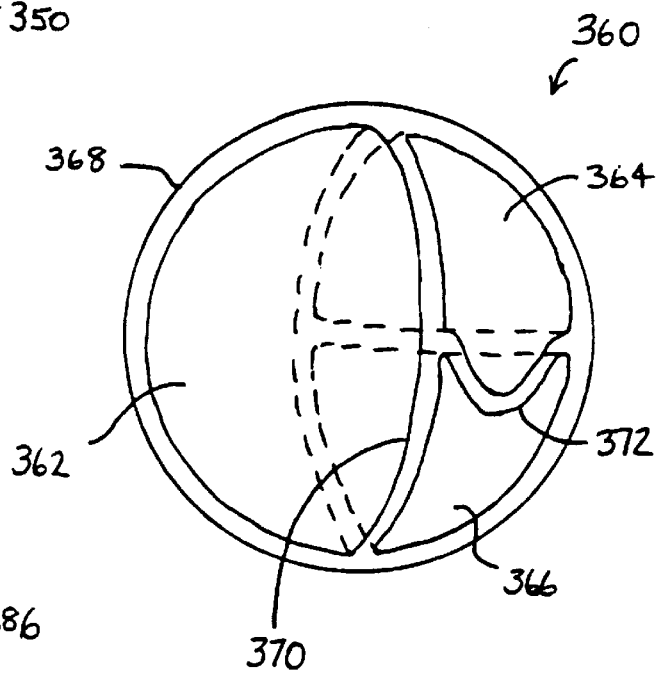
FIG. 14 is a sectional view of an alternative multi-lumen sheath for use in the present invention having a device lumen on one side and two stacked auxiliary lumens.

FIG. 14 is a further alternative cross-section of a sheath portion 360 for the multiple lumen access device for use with the present invention. The embodiment of FIG. 14 is similar to that shown in FIG. 13, and includes a device lumen 362, first auxiliary lumen 364, and second auxiliary lumen 366, all defined with an outer tube 368. In contrast to the embodiment of FIG. 13, the auxiliary lumens 364 and 366 are not arranged side-by-side, but are instead stacked on top of one another (at least in the orientation shown) so that both are located adjacent the device lumen 362. In this respect, a generally T-shaped internal dividing wall is provided including an elongated wall portion 370 and a shorter wall portion 372. The shorter wall portion 372 separates the first and second auxiliary lumens 364,366, while the elongated wall portion 370 separates the two auxiliary lumens from the device lumen 362. Both the elongated wall portion 370 and the shorter wall portion 372 are curvilinear in their relaxed configurations, shown in solid line in FIG. 14. The wall portions 370 and 372 straighten out into the dashed-line positions upon an increase in pressure in one or both of the auxiliary lumens 364, 366 relative to the device lumen 362.

In another alternative embodiment, not illustrated, the device lumen can be provided between two or more auxiliary lumens of different sizes. The device lumen is typically positioned off-center between crescent-shaped auxiliary lumens, and at least one of the auxiliary lumens can be expandable in accordance with the preceding discussion (that is, a wall between one of the auxiliary lumens and the device lumen is flexible). Desirably, there are two auxiliary lumens and the larger of the two lumens is expandable to enable infusion of large flow rates. In one particularly preferred embodiment, the larger lumen has a capacity equivalent to a gravity flow through a 14 gauge lumen.

Figure 15:
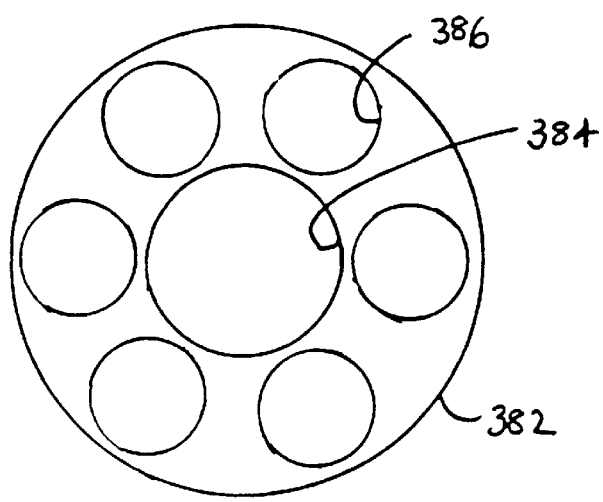
FIG. 15 is a sectional view of an alternative multi-lumen sheath for use in the present invention having no flexible walls therein.

FIG. 15 illustrates a still further cross-sectional view of a sheath portion 380 which may be used in conjunction with the multiple lumen access device for use with the present invention. In this embodiment, the sheath portion 380 includes a generally cylindrical solid member 382 having a central device lumen 384 and a plurality of auxiliary lumens 386 surrounding the device lumen formed therein. There are no flexible walls in this embodiment, it being understood that various aspects of the present invention may be advantageously utilized without the need for varying the cross-sectional shape of any of the lumens within the sheath portion 380. Alternatively, if desired, any wall portion separating the device lumen 384 from any of the auxiliary lumens 386 may be formed to be flexible to enable variability of the cross-section of that lumen.

Figure 12:
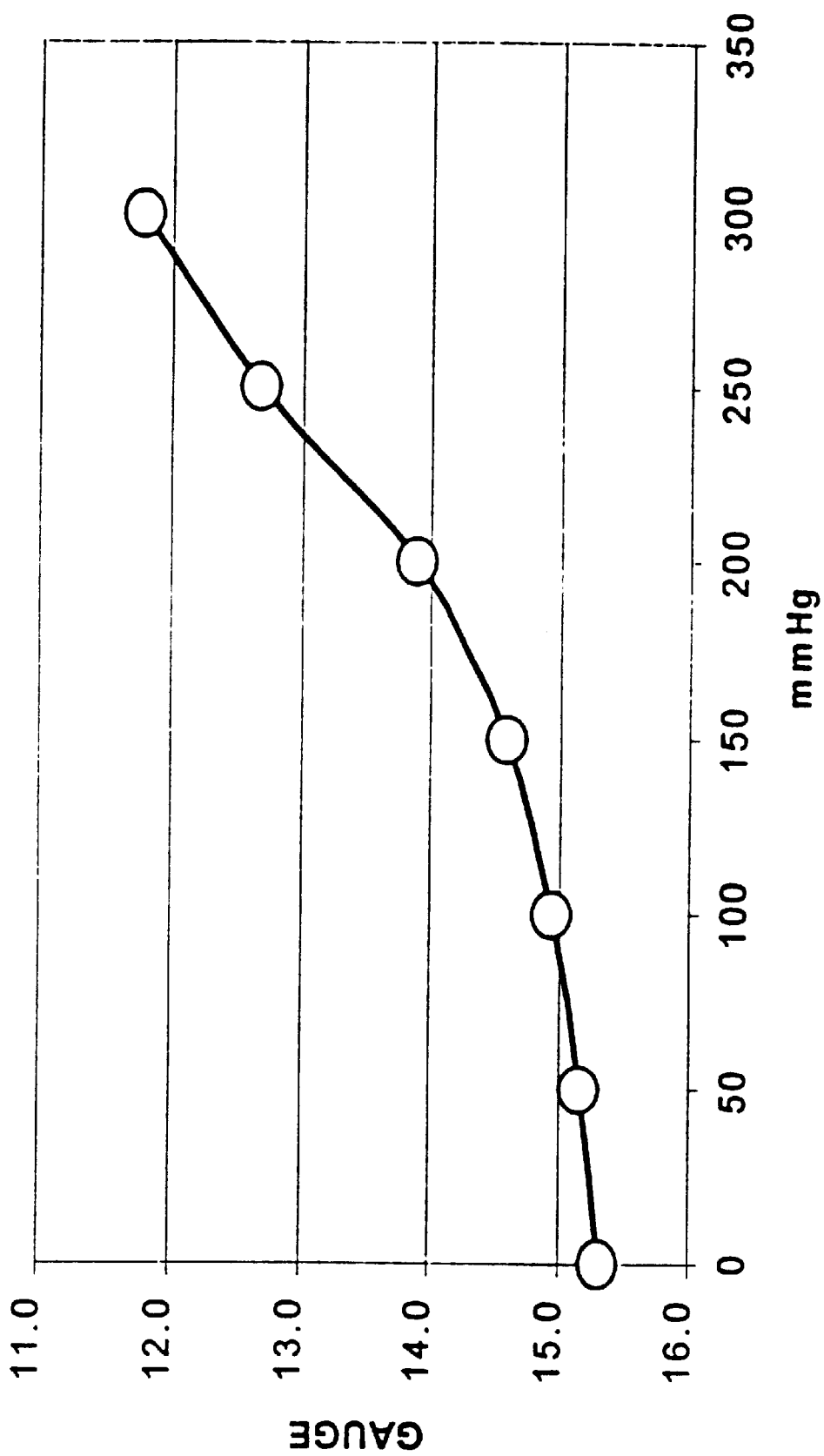
FIG. 12 is a graph illustrating an increase in the cross-sectional area (in gauge size) of an auxiliary lumen, such as in the cross-section shown in FIGS. 11A–11C, as the differential pressure between the auxiliary lumen and the device lumen changes.

The graph illustrated in FIG. 12 shows that as pressure inside the auxiliary lumen increases the cross-sectional area of that lumen increases. (The convention is that cross-section in terms of "gauge" numbers actually decreases for larger areas). FIG. 12 reflects the pressure response of one exemplary multi-lumen catheter wherein the auxiliary lumen increases in size from about 15 gauge when there is no flow therethrough, to about 12 gauge with fluid infusion at a pressure of about 300 mmHg (in this sense, the 300 mmHg is the differential pressure across the flexible wall, if the assumption is made that the device lumen is at atmospheric pressure). The response curve of the increase in lumen size indicates that the flexible wall is sufficiently rigid to withstand small changes in pressure. From 0–150 mmHg, the auxiliary lumen increases only from slightly smaller than 15 gauge to slightly larger than 15 gauge. Only above 150 mmHg pressure differential does the lumen size significantly increase. This response is a factor of the thickness, shape and material of the flexible wall between the device and auxiliary lumens.

One of the advantages of having an inner wall 25 (as seen in FIG. 11A) or inner wall 350 (as seen in FIG. 13) which is flexible but also sufficiently rigid is that a pressure transducer may be connected to the multi lumen access device of the present invention to monitor a central venous pressure of a patient. In particular, the pressure transducer (not shown) may be placed in communication with one of the auxiliary lumens 37 and 49 to measure the central venous pressure. Advantageously, the resistance to small pressure differentials described above enables more accurate pressure monitoring, because the flexible wall does not substantially flex upon small differentials in pressure, and thus does not dampen or attenuate the resultant pressure wave sensed externally to the lumen. Specifically, the flexible inner walls 25 have sufficient stiffness to avoid significant damping or attenuation of pressure pulses in the auxiliary lumens 37 and 49, and do not undergo major flexing from small pressure differentials as shown in FIG. 12.

As described previously in regards to the exemplary embodiment illustrated in FIGS. 1–5, the outer wall 15 of the embodiment illustrated in FIGS. 11A–11C is preferably made from any of the well-known polymer materials used in fabricating introducers and other access devices. Preferably, the material used and wall thickness for the outer wall 15 are such that the outer wall 15 is a relatively stiff tube in relation to the inner walls 25 in the radial direction. Further, the material used for the outer wall 15 should be compatible for molding purposes with the material used to form the inner walls 25. It is preferred that the entire cross-section of the multi-lumen portion of the device 10, including the outer tube 12 and inner walls 25, is extruded together from a homogeneous material. Alternatively, the outer wall 15 and inner walls 25 may be coextruded and that the junctions 27 be formed by molding of the inner 25 and outer wall 15 together during the coextrusion process. Therefore, outer wall 15 and inner walls 25 may be made from the same material or different materials. The inner wall 25 is preferably made from softer versions of the various polymers listed previously. When using different materials, the materials should be compatible for bonding or fusing together.

FIG. 16 illustrates an alternative multiple lumen device 400 (MLAD) for use with the present invention with an improved junction housing 402. The device 400 is similar to the FIGS. 1–5, and includes a multiple lumen sheath 404 extending distally from the housing 402. The multiple lumen sheath has a distal end 406 for insertion in a body cavity and a proximal end 408 attached to the housing 402. A plurality of extension tubes 410 is attached to the proximal end of the housing 402 and terminate in luer connectors 412. The housing comprises a valve insert portion 414 and a low profile lumen portion 416. A valve insert 418 is secured in a cavity defined in the portion 414. A pair of mounting wings 420 is integrally formed with the junction housing 402 for attaching to a patient.

The multiple lumen sheath 404 seen in cross-section in FIG. 17 comprises an outer circular tube 422 having an interior surface 424. In the illustrated embodiment, the multiple lumen sheath 404 includes a central device lumen 426 and a pair of auxiliary lumens 428 disposed on opposite sides of the device lumen. The device lumen 426 is defined between interior surfaces 430 of a pair of divider walls 432. The divider walls extend in a non-linear fashion substantially across the entire outer tube 422 and terminate at junctions 434. The junctions 434 are spaced a slight distance from one another so that the sheath 404 does not exhibit the separation barriers, as previously described. As illustrated, the device lumen 426 is generally concentrically positioned within the outer tube 422 and has a nominal diameter of slightly greater than half the outer tube 422. Between exterior surfaces 436 of the divider walls 432 and the interior surfaces 424 of the outer tube 422, the auxiliary lumens 428 are formed. The lumens 428 are substantially crescent shaped and are shown identical in size. Of course, as described previously, various other lumen configurations can be provided in the multiple lumen sheath 404.

Again, although the device 400 includes a device lumen valve insert 418 that is incorporated into the junction housing 402 (and is thus non-detachable during use of the device), it also includes a plurality of extension tubes 410 that can be modified to include the safety valve of the present invention, as described below with respect to FIGS. 23–27. Therefore, the combination of various aspects of the device 400 and the safety valve is within the scope of the present invention.

Figure 19:
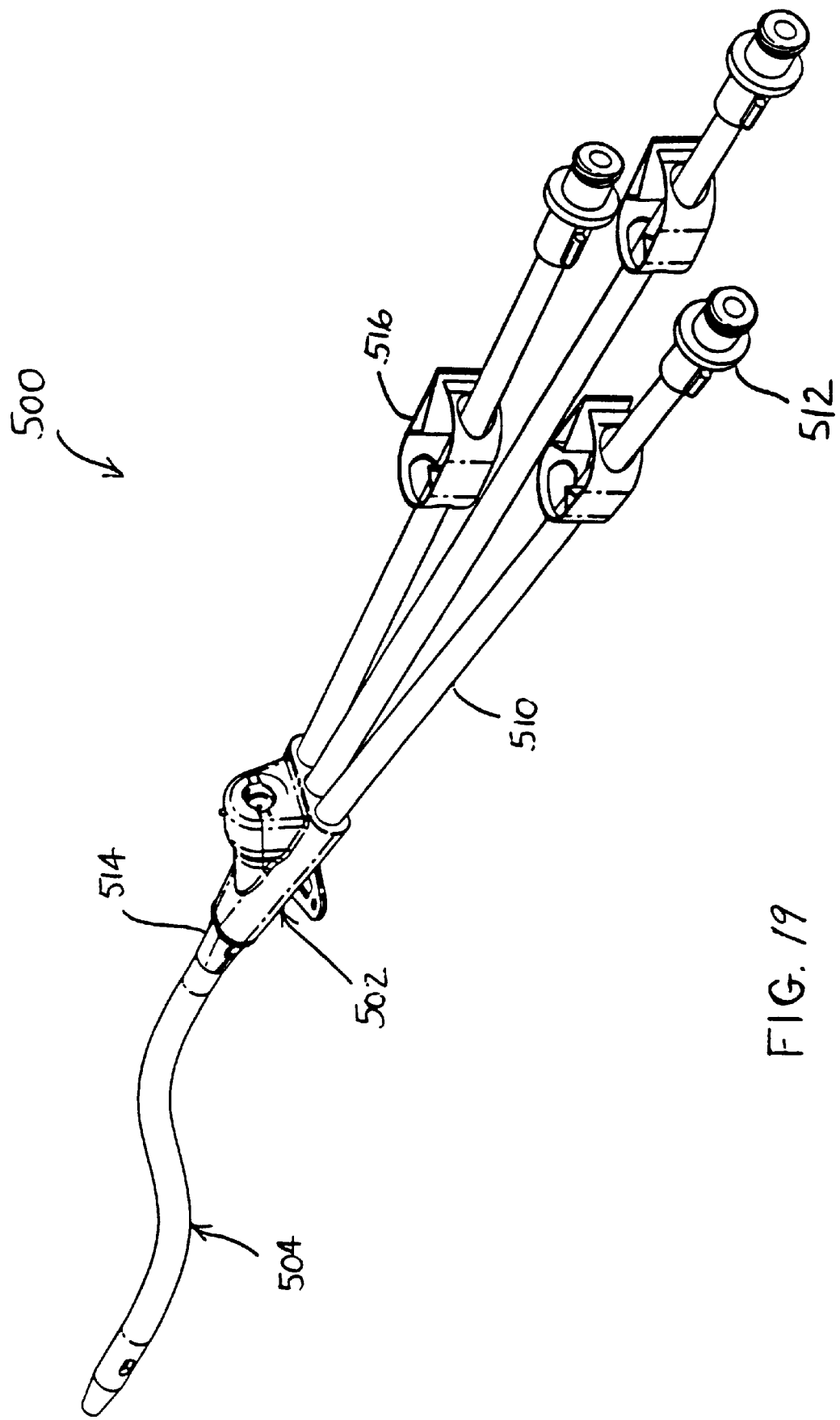

FIGS. 18 and 19 are different perspective angles of an exemplary multiple lumen access device 500 for use with the present invention, which is in many respects very similar to the device 400 shown in FIG. 16. The device 500 includes a junction housing 502, a distal sheath 504, and a plurality of proximal extension tubes 510 terminating in luer connectors 512. One of the main distinctions from the earlier described embodiment is the provision of a strain relief insert 514 positioned at the distal end of the junction housing 502.

Figure 20:
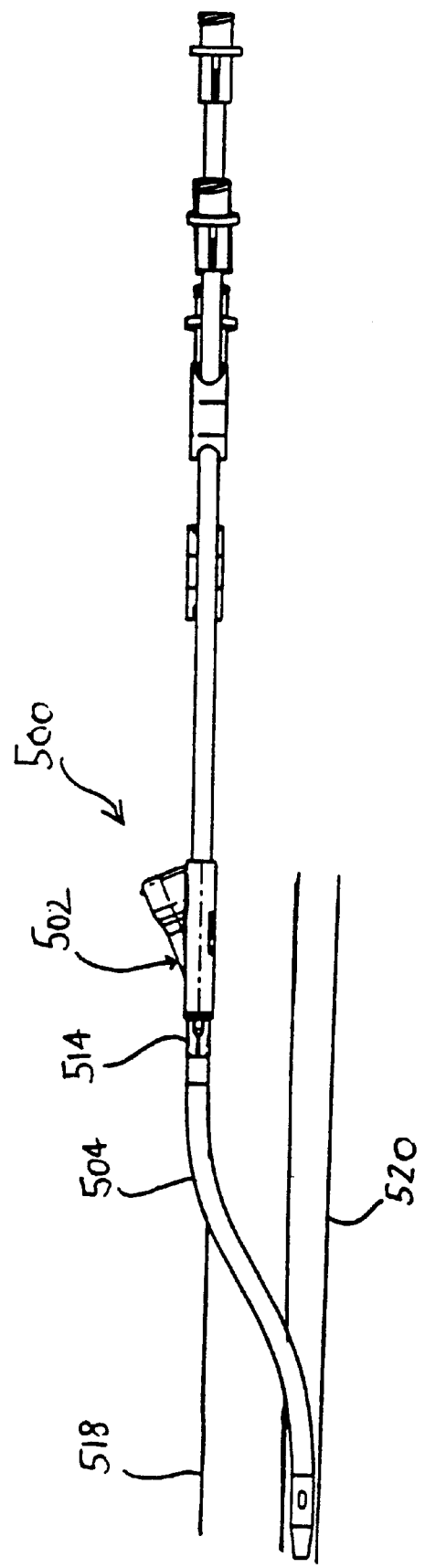
FIG. 20 is an elevational view of the multiple lumen access device of FIGS. 18 and 19 in place in the vasculature of a patient.

FIG. 20 shows a side elevational view of the device 500 showing the distal sheath 504 inserted through the outer tissue 518 of a patient and into a vessel 520. The flexible nature of the sheath 504 is seen in this figure, as well as the ability of the junction housing 502 to live flat against the patient's skin.

Figure 21:
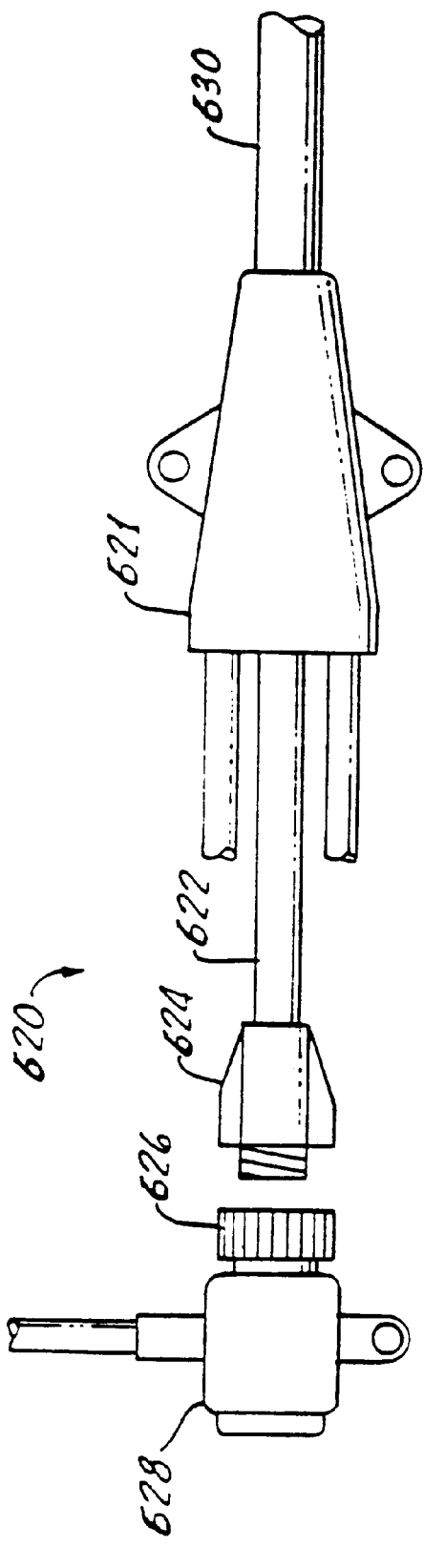
FIG. 21 is a plan view of an alternative multiple lumen access device with a low profile junction housing.
Figure 22:
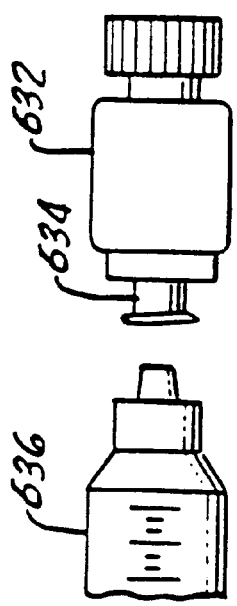
FIG. 22 is a detailed view of an alternative introducer valve assembly for use in the device of FIG. 21.

FIG. 21 illustrates a further embodiment of the multiple lumen access device 600 in which the device access valve is not formed integrally with a junction housing. More particularly, a multiple lumen access device 620 includes a central extension tube 622 that terminates in a luer connector 624. The luer connector 624 is desirably used to mate with a female luer connector 626 of an introducer valve assembly 628. However, in this detachable configuration, various other medical devices having conventional luer fittings may be attached to the luer connector 624 and placed in communication with a central lumen of the multi-lumen sheath 630. FIG. 22 illustrates a further alternative, wherein the introducer valve assembly 632 is provided with a male luer connector 634 on a proximal end to which an infusion syringe 636 maybe attached. As can be seen, various configurations are possible with the remote introducer valve assembly 628, and the low profile junction housing 621 is easily molded over the extension tubes and has a reduced size, thus facilitating the manufacturing process.

Access Device of the Present Invention with Remote Introducer Valve & Hemostatic Safety Valve FIGS. 23–27 show embodiments of a vascular access device 640 of the present invention having a detachable device lumen valve or device access valve 628a. The device access valve 628a may be similar or identical to the remote introducer valve assembly 628 described above with respect to FIG. 21. A hemostatic safety valve 642 is provided on the proximal end of the device lumen to prevent blood from backflowing out of the device lumen when the device access valve 628a is purposely or inadvertently detached therefrom. The inventive combination of a device valve and a hemostatic safety valve assembly for use with a vascular access device may be used with a multiple lumen access device, for example, as one shown in FIG. 23, or it may be used with a single lumen access device, such as an introducer or a central venous catheter. Therefore, descriptions of the present invention with respect to the multiple lumen access device is equally applicable to the standard single lumen access devices.

The Multiple Lumen Access Device With Hemostatic Safety Valve

As shown in FIGS. 23, 24 and 25, the multiple lumen access device 640 comprises a multiple lumen sheath 630a having a junction housing 621a formed on the proximal end thereof A plurality of extension tubes 622a, 622b extend from the junction housing 620, the central extension tube 622a being connected to the device lumen of the sheath 630a through which guidewires, catheters and other devices (represented by the tube 643 in FIGS. 24 and 25) are intended to be inserted. The other extension tubes 622b are connected to other lumens of the sheath 630a to facilitate infusion of liquids through those other lumens.

In this embodiment, the hemostatic safety valve 642 is mounted or otherwise provided on the proximal end of the central extension tube 622a. The hemostatic safety valve 642 comprises a rigid body 644 having a hollow bore 646 (FIG. 25) extending therethrough and an externally threaded male Luer connector 648 on the proximal end thereof An elastomeric membrane 650 is mounted transversely over the proximal end of the body 644 in a manner that occludes or blocks its hollow bore 646. A self-sealing slit 652 is formed in the center of the elastomeric membrane 650. The slit 652 is biased to a closed or sealed configuration such that, so long as the elastomeric membrane 650 remains un-stretched, the slit 652 will remain closed and blood will be thereby prevented from leaking out of the proximal end of the hemostatic safety valve 642.

The hemostatic safety valve 642 is desirably molded or adhesively fastened onto the proximal end of the central extension tube 622a, as seen in FIG. 26. In this way, the hemostatic safety valve 642 remains attached to the extension tube 622a at all times. Alternatively, an off-the-shelf hemostatic safety valve 642, such as are available from the IV Systems Division of Baxter International, Inc., may be semi-permanently engaged with a male luer connector 654 (as seen, for example, in FIG. 23) on the extension tube 622a through the use of adhesives on the mating threads. Other such valves may be obtained from Halkey-Roberts of St. Petersburg, Fla., as a modification of part No. 24500420, or from Vernay Laboratories, Inc., P.O. Box 310, Yellow Springs, Ohio. As mentioned, those valves all are designed to seal a device lumen, which is typically larger than an infusion lumen, at greater pressures than the device valve is designed to seal.

The term "semi-permanently engaged" is intended to cover those configurations in which the hemostatic safety valve 642 cannot be removed, either deliberately or accidentally, by hospital personnel or the patient, without significant effort and perhaps damage to the operational aspects of the device. This can also be termed "non-detachably secured". Thus, a threaded and adhesively fastened connection could theoretically be separated using pliers, or the like, but is not intended to be so separated.

Examples of Detachable Device Lumen Valves

It will be appreciated that various types of detachable device lumen valves may be used with this embodiment of the invention. One particular type of device lumen valve 628a is shown in FIGS. 23–26 while another particular type of device lumen valve 628b is shown in FIG. 27.

With specific reference to FIGS. 23–26, one type of detachable device lumen valve 628a comprises a distal body member 660, a duckbill valve 662, first, second and third elastomeric disks 664, 666, 668, each having a hole in the center, and a proximal body member 670. The elastomeric disks 664, 666, 668 may be made of silicone, of various conventional designs. The distal body member 660 is formed of hard plastic and generally has a female Luer configuration on its distal end with internal threads for mating with the externally threaded male Luer connector 648 of the hemostatic safety valve 642. A hollow male projection 674 extends concentrically within the distal end of the distal body member 660 and projects slightly distally outward therefrom. A proximal portion 676 of the distal body member 660 is of reduced diameter and is externally threaded to mate with the proximal body member 670 as seen in FIG. 25. A hollow bore 678 extends longitudinally through the distal body member 660. The proximal body member 670 is also formed of hard plastic, is internally threaded and has a hollow bore 680 extending longitudinally therethrough.

When the valve 628a is assembled, the proximal portion 676 of the distal body member 660 is rotationally advanced and received within the internally threaded cavity of the proximal body member 670 so as to capture the duckbill valve 662, and disks 664, 666, and 668 in a stacked array between the proximal body member 670 and the distal body member 660.

The detachable device lumen valve 628a having the male projection 674 formed thereon is attachable to the safety valve 642. When so attached (see FIG. 25) the male projection 674 of the device lumen valve 628a protrudes into or through and stretches the elastomeric membrane 650, thereby causing the self-sealing slit 652 to be opened or at least aligned with the bore 678 of the device lumen valve 628a such that a guidewire, catheter or other device 643 that is advanced through the device lumen valve 628a may continue to advance through the elastomeric membrane 650, through the central extension tube 622a and through the device lumen of the multiple lumen sheath 630a.

When a catheter, guidewire or other device 643 is advanced through the device lumen valve 628a, it passes through the bore 680 of the proximal body member 670, through the holes in the centers of the disks 664, 666 and 668. Then, after having advanced through the silicone disk 664, the catheter, guidewire or other device presses against the distal side of duckbill valve 662 causing the leaflets of the duckbill valve 662 to separate and allowing the catheter, guidewire or other device to pass on through the bore 678 of the distal body member 660, through the slit 652 of the elastomeric membrane 650 (FIG. 26) and on through the central extension tube 622a and device lumen. A fluid infusion side port 681 is formed on the distal body member 660 to permit infusion of liquid through the device lumen when no device is positioned therein and/or the infusion of liquid around a device that has already been inserted through the device lumen for the purpose of providing lubricity or otherwise facilitating the advancement and positioning of the device.

When the device lumen valve 628a is detached from the proximal end of the safety valve 642, the elastomeric membrane 650 will no longer be stretched and the self-sealing slit 652 will resiliently return to its closed or sealed configuration. In this manner, the elastomeric membrane 650 will fully occlude the bore of the safety valve 642 to prevent blood from backflowing in the proximal direction out of the safety valve 642 when the device lumen valve 628a, 628b is purposely or inadvertently detached. The elastomeric membrane 650 is of a stiffer material and/or thicker configuration so that most guidewires and smaller catheters that are relatively flexible cannot pass through the slit 652. Such membranes 650 are sometimes referred to as septums, and are typically use in fluid sampling ports designed for puncture by a blunt-tipped syringe. The stiffness of the membrane 650 prevents a technician from inadvertently passing flexible catheters or guidewires into the vasculature without the device lumen valve 628a being present. The male projection 674 of the device lumen valve 628a is required for passage of such flexible catheters, which projection holds the membrane 650 open and thus only the more compliant disks 664, 666, 668 and duckbill valve 662 need be pierced.

With particular reference to FIG. 27, another type of detachable device lumen valve 628b is generally known in the field as a Touhy Borst valve. This Touhy Borst type device lumen valve 628b comprises a distal body member 682, a duckbill valve 684, a compressible O-ring 686 and a proximal body member 688. The distal half of the distal body member 682 is formed of hard plastic and generally has a female Leur configuration with internal threads (not shown) and a male projection 692. A proximal portion 694 of the distal body member 682 is of reduced diameter and is externally threaded, as shown. A hollow bore 696 extends longitudinally through the distal body member 682. The proximal body member 688 is also formed of hard plastic, is internally threaded and has a hollow bore 698 extending longitudinally therethrough.

When this valve 628b is assembled, the proximal portion 676 of the distal body member 660 is rotationally advanced and received within the internally threaded cavity of the proximal body member 670 so as to capture the duckbill valve 684 and compressible O-ring 686 therebetween. The proximal body member 688 remains rotatable on the distal body member 682 so that the compressive force exerted on the compressible O-ring 686 may be changed by rotatably advancing or retracting the proximal body member 688 relative to the distal body member 682. In this manner, when the proximal body member 688 is fully advanced the O-ring 686 will be compressed such that the diameter of the hole in its center will be minimized. However, when the proximal body member 688 is retracted, the O-ring 686 will be decompressed and the diameter of the hole in its center will enlarge. This allows the valve 628b to be adjusted so that its O-ring 686 will seal about the outer surfaces of guidewires, catheters and other devices of varying diameter.

The detachable device lumen valve 628b having the male projection 692 formed thereon is attachable to the safety valve 642. When so attached (similar to FIG. 26) the male projection 692 of the device lumen valve 628b protrudes into and stretches the elastomeric membrane 650, thereby causing the self-sealing slit 652 to be opened or at least aligned with the bores 696, 698 of the device lumen valve 628b such that a guidewire, catheter or other device that is advanced through the device lumen valve 628b may continue to advance through the elastomeric membrane 650, through the central extension tube 622a and through the device lumen of the multiple lumen sheath 630a. However, when the device lumen valve 628b is detached from the proximal end of the safety valve 642, the elastomeric membrane 650 will no longer be stretched and the self-sealing slit will resiliently return to its closed or sealed configuration. In this manner, the elastomeric membrane 650 will fully occlude the bore of the safety valve 642 to prevent blood from backflowing in the proximal direction out of the safety valve 642 when the device lumen valve 628b is purposely or inadvertently detached.

When a catheter, guidewire or other device is advanced through the device lumen valve 628b, the proximal body member 688 will be loosened (i.e., unscrewed slightly) and the guidewire, catheter or other device will be advanced through the bore 698 of the distal body member 682 and through the hole in the O-ring 686. Then, after having advanced through O-ring 686, the catheter, guidewire or other device presses against the distal side of duckbill valve 684 causing the leaflets of the duckbill valve 684 to separate and allowing the catheter, guidewire or other device to pass on through the bore 696 of the distal body member 682, through the slit 652 of the elastomeric member 650 (FIG. 26) and on through the central extension tube 622a and device lumen. A fluid infusion side port 699 is formed on the distal body member 660 to permit infusion of liquid through the device lumen when no device is positioned therein and/or the infusion of liquid around a device that has already been inserted through the device lumen for the purpose of providing lubricity or otherwise facilitating the advancement and positioning of the device.

As will be understood by those skilled in the art, various combinations of the appropriate detachable device lumen valves and safety valves for use with the vascular access devices to prevent blood leakage are within the scope of the present invention.

The present invention further provides a method for introducing medical devices into the body through a single entry port while at all times preventing backflow of fluids through the entry port. An exemplary method of the present invention includes the steps of providing a vascular access device having a device lumen and a safety valve on the proximal end thereof, introducing the vascular access device into the body with the distal end of the device lumen being positioned within a vasculature of the body; attaching a detachable hemostasis valve to the safety valve to open the safety valve, and inserting a device through the hemostatis valve, open safety valve and device lumen. The vascular access device for use in the described method may be a single lumen access device, for example an introducer or a catheter, or instead, various multiple lumen access devices may be used.

Further examples of other vascular access devices, such as combinations of the various introducers and catheters, that can be used with the present invention are described below.

Access Device with Multiple Discrete Tubes

Figure 28:
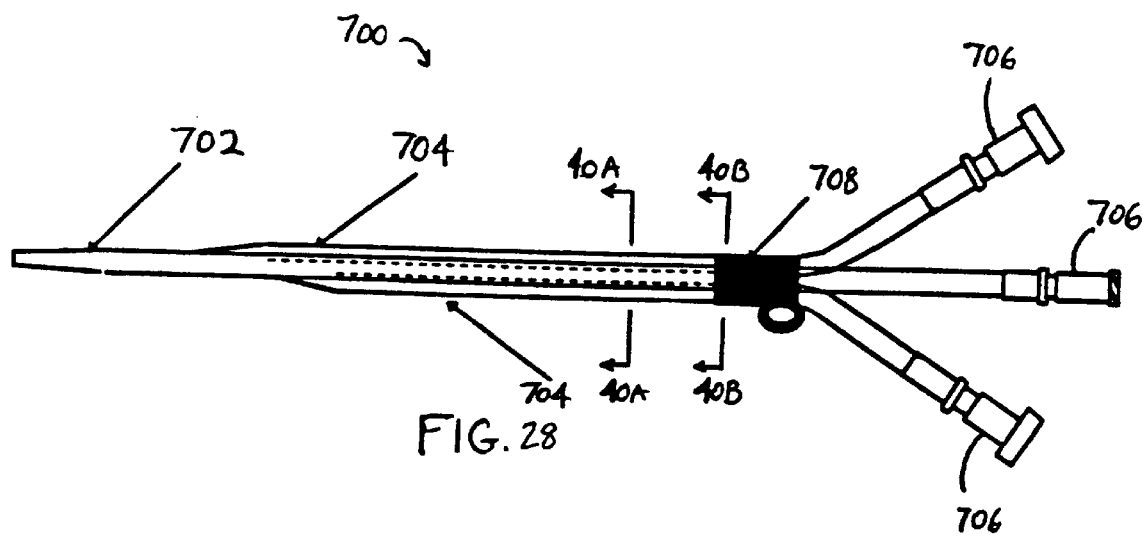
FIG. 28 is a plan view of a multiple lumen access device for use with the present invention having a center tube and two side lumen tubes in accordance with the present invention.
Figure 29A:
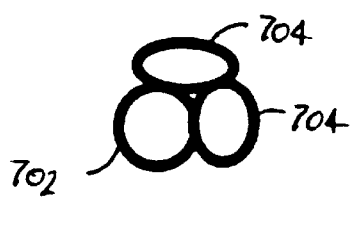
FIGS. 29A and 29B are sectional views of a sheath of the multiple lumen access device of FIG. 28 taken along lines 29A—29A and 29B—29B, respectively.
Figure 29B:
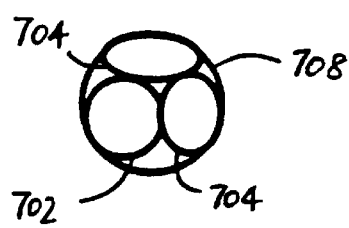

FIG. 28 illustrates a multi-lumen catheter device 700 having at least two discrete catheter tubes. In this embodiment, the multi-lumen catheter device 700 includes a main (or center) lumen tube 702 and two side lumen tubes 704. The lumen tubes 702 and 704 are configured in a side-by-side fashion, and proximal portions of the tubes 702, 704 are peeled apart to create sidearms. Hubs 706 may be attached to proximal ends of each lumen tube 702, 704 for fluid delivery or introduction of a medical device. Remote introducer valves may be connected to one or all the lumen tubes. Indeed, the device valves may be provided on any or all of the extension tubes for the various embodiments described herein and shown in any of the figures, including FIGS. 1, 6, 23A, 30. The catheter device 700 may further include a sleeve 708 at the region where the lumen tubes 702 and 704 branch outwardly. FIGS. 29A and 29B illustrate the different cross-sections of the device 700, the circular shape of the sleeve providing a smooth transition for sealing through a puncture wound into the skin. One of the advantages of this embodiment is that one or more of the lumen tubes 702 and 704 may be peeled off the multi-lumen catheter 700 if desired.

Figure 30:
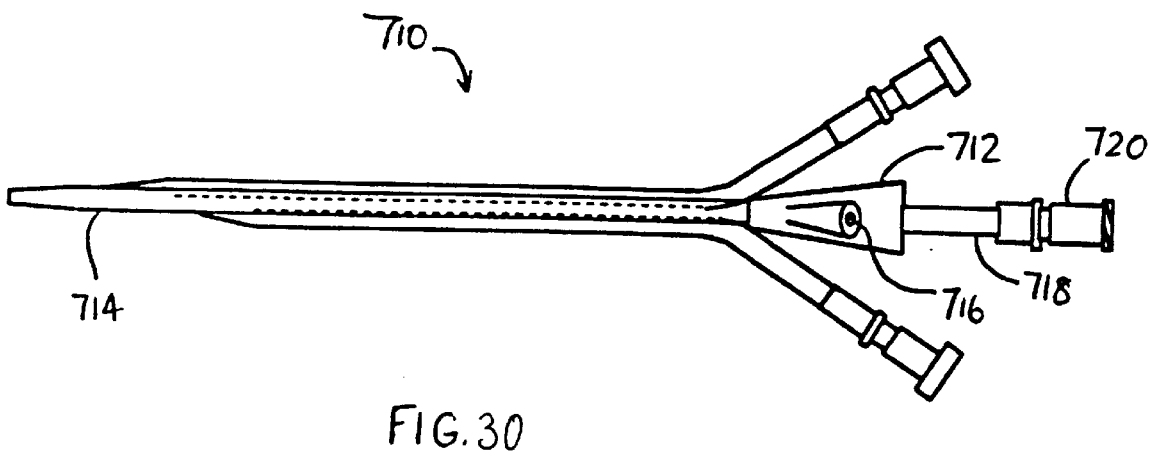
FIG. 30 is an alternative multiple lumen access device with discrete tubes as in FIG. 28 and having a junction housing.

FIG. 30 illustrates another alternative multi-lumen catheter device 710. This catheter device 710 is similar to the catheter device 700 illustrated in FIG. 28 and includes the additional feature of a junction housing 712 connected to a proximal end of a main lumen tube 714. The junction housing 712 receives a valve insert 716 and an extension tube 718 with a hub 720 connected to its proximal end. Again, the separate tubes can be peeled away to create various lumen devices.

Multiple Lumen Catheter Through Introducer

FIGS. 31A and 31B illustrate a multi-function adapter 730 for connecting different components, for example, catheters and introducers, for use with the present invention. The multi-function adapter include a first unit and a second unit that are complementary and enable a quick-release connection of a multiple lumen device and an introducer. By way of example and not limitation, the multi-function adapter may include a female unit 730a and a male unit 730b. The male unit 730b includes at least one lug 732 extending radially outward, while the female unit 730a includes a slot (not illustrated) which accepts and interlocks with the lug. The slot may be a variety of configurations to securely interlock the male unit with the female unit, such as an L-shaped channel, a bayonet lock, an interference fit, etc. Other types of adapters known in the art such as luers may be utilized as long as components of the access device can be easily connected/disconnected.

In the embodiment of FIGS. 31A and 31B, the adapter 730 couples a multiple lumen catheter 734 with an introducer 735. The catheter 734 may be a CCO catheter or other multiple-lumen device, and includes a junction housing 736 between a distal multi-lumen sheath 738 and a plurality of proximal extension tubes 740. The introducer 735 includes a hub 742 with a side arm 744 for introducing or withdrawing fluids. The female unit 730a is adapted to fit over the sheath 738 by a press fit, adhesive, or any other means generally known in the art. Conversely, the male unit may be fixedly attached to the sheath 738 or distal end of the junction housing 736 instead of the female unit, if desired. The adapter 730 permits detachability of the multiple lumen catheter 734 from the introducer 735 and provides great flexibility in surgical or critical care situations.

FIGS. 32A and 32B illustrate a multiple-lumen access device 760 very similar to the device of FIGS. 31A and 31B but with the adapter formed as part of a multiple lumen catheter junction housing. The access device 760 includes an introducer 762 connected to a Central Venous Catheter (CVC) or other multiple lumen catheter 764 by a multi-function adapter 766a and 766b. The catheter 764 includes a multiple-lumen sheath 768 connected to a junction housing 770.

The access device 760 (and the device of FIGS. 31) offers a significant advantage over current catheter designs in terms of cost saving and manner in which the access device 760 may be utilized. Currently, an introducer is inserted into a vein, and a surgical procedure is performed. After the surgical procedure, the introducer is usually removed and a new catheter is inserted in the vein through a second puncture and sutured onto the skin. The patient is then transported to a recovery room. By using the access device 760 illustrated in FIG. 32, the procedure can be greatly simplified. The introducer 762 is first positioned in the vessel using traditional methods, such as the Seldinger technique. After the introducer 762 is used for sampling or infusing fluids, multiple lumen catheter 764 is inserted and utilized. The catheter 764 can then be detached from the introducer 762 and removed from the vessel while the introducer 762 is left in the vessel, and the introducer 762 now functions as a catheter. Thus, after the surgical procedure, the introducer 762 does not have to be removed from the vessel and a new catheter does not have to be inserted through a second puncture.

Figures 33A, 33B:
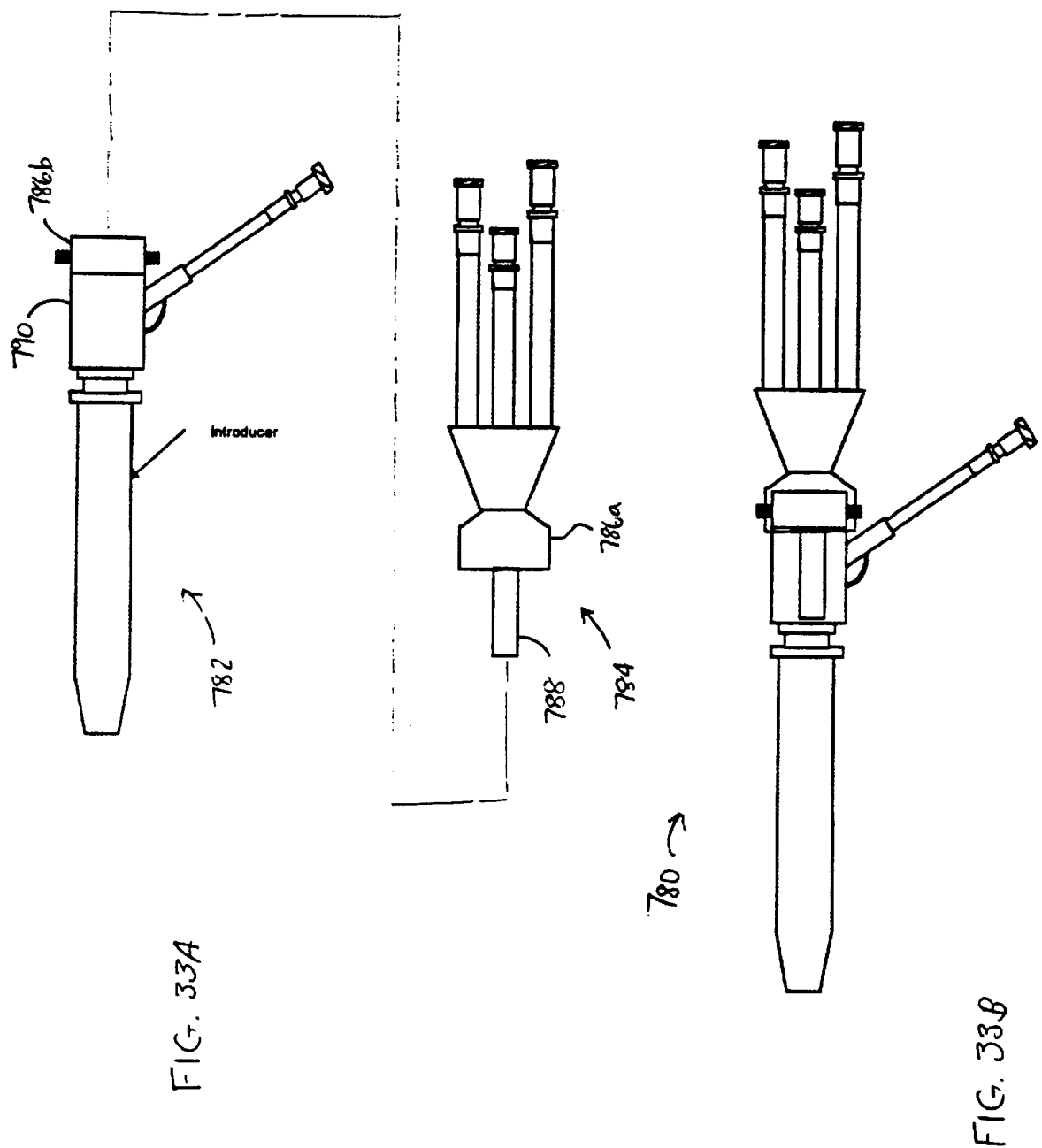
FIG. 33A is an exploded view of a multiple lumen access device having an introducer with infusion port connected to a triple lumen junction housing and obturator by an adapter.
FIG. 33B is an assembled view of the multiple lumen access device of FIG. 33A.

FIGS. 33A and 33B illustrate a multiple lumen access device 780 having an introducer 782 connected to a triple lumen junction housing 784 by a multi-function adapter 786a and 786b. Instead of the elongated sheath as in the previous two embodiments, the junction housing 784 includes a short hollow obturator 788 that serves to hold open a hemostasis valve in a hub 790 of the introducer 782. The three lumens within the junction housing 784 communicate with the lumen of the obturator 788 to deliver fluids to the introducer lumen.

FIGS. 34A and 34B illustrate an access device 820 having a single lumen introducer 822 connected to a multiple lumen junction housing 824by a threaded female adapter 826 and male luer connection 828. A device valve 830 in the junction housing 824 permits insertion of various devices into a vessel via the introducer 822 at the same time that various fluids are infused through extension tubes 832.

FIGS. 35A and 35B illustrate an access device 840 similar to the access device 820 illustrated in FIG. 34 and includes the additional feature of a small diameter catheter tube 842 extending from a distal end of ajunction housing 844. The catheter tube 842 functions as an infusion lumen for one of the extension tubes 846, while the space between the catheter tube 842 and a single lumen introducer 848 functions as a device lumen. Again, the junction housing 844 is attached to the introducer 848 with a threaded adapter 850.

Introducer Within Introducer Combination

Figures 36A, 36B:
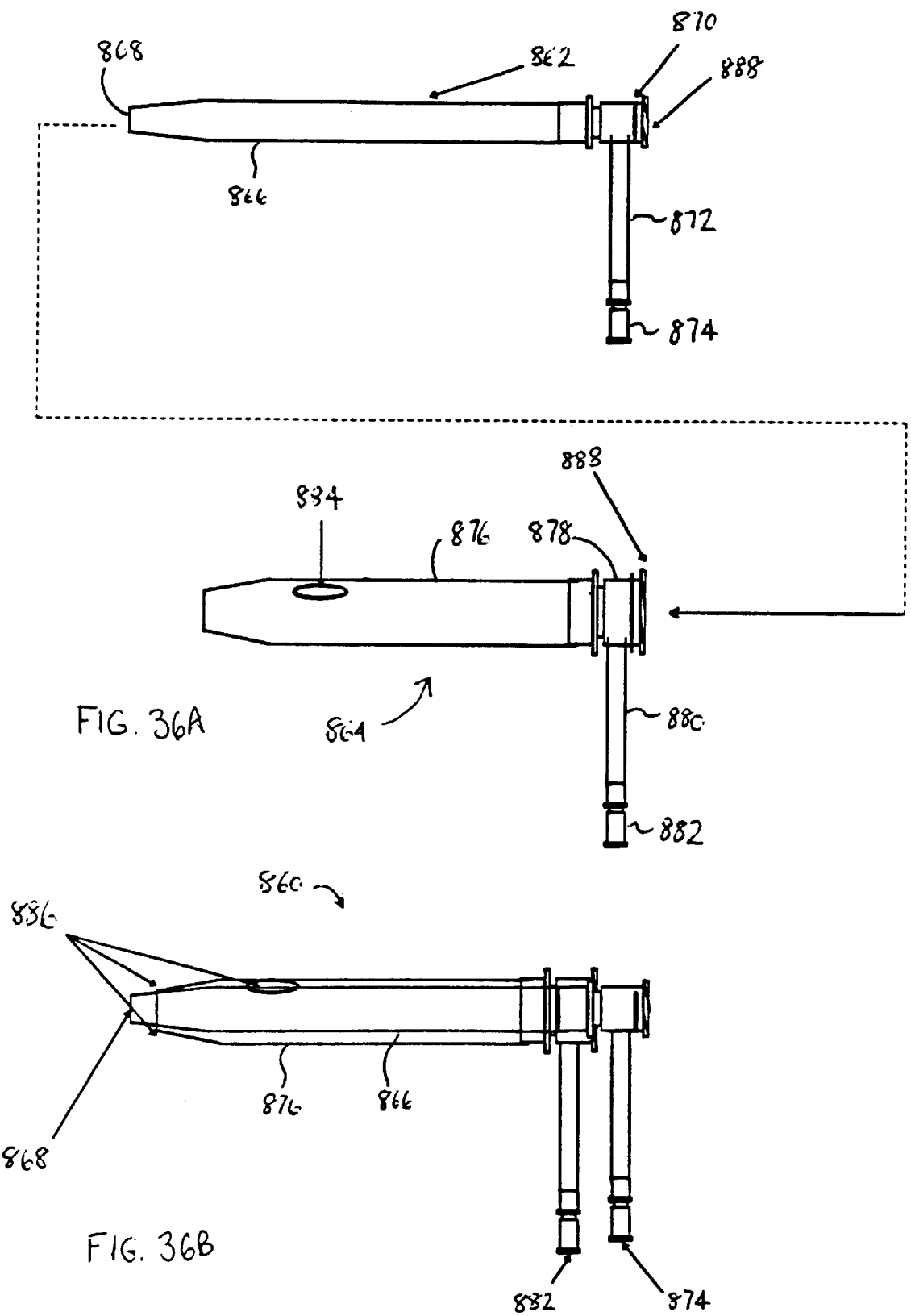
FIG. 36A is an exploded view of a multiple lumen access device having an introducer with infusion port telescopically fitting within a larger introducer.
FIG. 36B is an assembled view of the multiple lumen access device of FIG. 36A.

A multiple lumen access to the body through a single patient entrance site may also be accomplished by using a plurality of elongated sheaths and implements, such as introducers, obturators or catheters, inserted coaxially within each other to form multiple independent lumens. FIGS. 36A and 36B, for example, illustrate a multi-lumen access device 860 comprising a first single-lumen introducer 862 telescopically received within a second single-lumen introducer 864. The first introducer 862 includes a single lumen sheath 866 having an opening 868 at its distal end and connected to an introducer valve housing 870 at its proximal end. Within the introducer valve housing, a duck-billed valve or other appropriate valves may be provided to seal the lumen from the exterior. The introducer valve housing 870 may include a side port extension tube 872 terminating in a hub 874 for attaching to infusion fluid sources. The second elongated implement, for example, an introducer 864 includes a single lumen sheath 876 connected to the distal end of an introducer valve housing 878. The introducer valve housing 878 also may include a side port extension tube 880 terminating in a hub 882 for attaching to infusion fluid sources, and the sheath 876 may include an opening 884 towards a distal end thereof to allow exit of fluid which has been introduced through the side port extension tube 880.

As shown in FIG. 36B, the sheath 866 of the first introducer 862 is sized to fit coaxially through the introducer valve 878 and lumen of the second introducer 864. The distal opening 868 of the first introducer sheath 866 may extend beyond the distal end of the second introducer sheath 876. In addition, at least one of the lumens formed by the placement of introducer 862 coaxially within the introducer 864 is capable of passing a supplemental catheter. By way of example and not limitation, one such catheter has an outside diameter sized about 4 French or more. In one exemplary application of FIG. 36B, fluid 1 (for example, medicine 1) may be introduced through the hub 882 and may exit the device through the opening 884 while fluid 2 (for example, medicine 2) may be introduced through the hub 874 and exit the device through the opening 868. Alternatively, the fit between the smaller sheath 866 and larger sheath 876 may be somewhat loose at the distal end so that fluid introduced through hub 882 may pass through an annular space formed therebetween, and through the opening 884, as indicated by the arrows 886. Both introducers 862 and 864 include male luer connectors 888 on their proximal ends for connecting to a variety of medical implements, including the threaded adapters for attaching multiple lumen catheters as previously described.

The access device 860 offers a significant advantage over known introducers by providing multiple lumen access with only a single patient entrance site. Currently, two introducers are usually inserted into the patient at two different sites if another independent lumen is required. The access device 860 allows the flexibility to start a procedure with only one introducer 864, and if another independent lumen is required, an additional introducer 862 can be inserted into the introducer 864. It is noted that the access device is not limited to two introducers. For example, a combination of three or more introducers may be coaxially configured if additional independent lumens are required.

Also, as will be understood by those skilled in the art, at least one of the single lumen introducers that is coaxially inserted into another single lumen introducer may be made from a flexible deformable material. As a result, the wall forming the sheath of such insertable introducer will also form at least one of the multiple lumens and will be movable upon differential changes in pressure across the wall. This follows from the principles described earlier with respect to extruded multiple lumen sheaths, including the descriptions related to FIGS. 3A–B, 11A–C, 12 and 17. For instance, the larger introducer sheath 876 may be rigid, while the smaller introducer sheath 866 may be flexible or pliable. If a large amount of fluid is infused through larger introducer hub 882, the space around the smaller sheath 866 experiences an increase in pressure and the sheath may buckle inward to accommodate the larger flow. In one embodiment, a portion of the inside introducer may be rigid and some portion may be flexible, for example only the distal tip of the smaller introducer is rigid to permit insertion through the larger introducer.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

What is claimed is:

1. A vascular access system for use in providing an entry port into the human body, comprising:

an outer tube which has a distal end for introduction into the body, a device lumen being defined within the outer tube, the device lumen having a distal end and a proximal end, wherein medical devices may be passed through the device lumen;

a hemostatic safety valve non-detachably secured on the proximal end of the device lumen to prevent leakage of blood from the device lumen;

a detachable device lumen valve attachable to the proximal end of the hemostatic safety valve to open the hemostatic safety valve and allow passage of an elongate device through the device lumen while preventing leakage of blood therefrom.

2. The system of claim 1, further including:

a junction housing having a proximal end and a distal end and located between the outer tube and hemostatic safety valve, the junction housing having an internal channel in communication with the device lumen; and an extension tube attached to the proximal end of the junction housing, the hemostatic safety valve being secured to the free end of the extension tube.

3. The system of claim 2, wherein the junction housing further includes at least one auxiliary channel in fluid communication with at least one auxiliary lumen defined within the outer tube, separate from the device lumen, the main channel and auxiliary channel diverging from the outer tube to be non-intersecting in the junction housing.

4. The system of claim 3, further including a second extension tube attached to the proximal end of the junction housing in fluid communication with the auxiliary channel.

5. The system of claim 4, further including at least one flexible wall located within the outer tube having a distal end and a proximal end and opposite sides, wherein one side of the wall partly defines the device lumen and the other side of the wall partly defines the auxiliary lumen, the wall being sufficiently flexible to be movable from a relaxed position wherein the device lumen has a first cross-sectional area to flexed positions wherein the device lumen has cross-sectional areas which are greater than or less than the first cross-sectional area and less than the cross-sectional area of the outer tube.

6. The system of claim 1, wherein the detachable device lumen valve comprises a distal body member and a proximal body member threadingly connected together and housed within an elastomeric valve member.

7. The system of claim 6, wherein the elastomeric valve member comprises a duckbill valve.

8. The system of claim 7, wherein the elastomeric valve member further comprises first, second and third elastomeric disks each having a hole in the center.

9. The system of claim 7, wherein the elastomeric valve member further comprises a compressible O-ring having a central hole with a size that can be changed by rotatably advancing or retracting the proximal body member relative to the distal body member.

10. The system of claim 1, wherein the hemostatic safety valve includes an elastomeric valve member, and the detachable device lumen valve comprises an elastomeric valve member that is more compliant than the elastomeric valve member of the hemostatic safety valve so as to enable introduction of guidewires and flexible catheters through the detachable device lumen valve.

11. The system of claim 1, wherein the hemostatic safety valve includes an elastomeric valve member, and the detachable device lumen valve has a distally-directed projection that opens the elastomeric valve member of the hemostatic safety valve.

12. The system of claim 11, wherein the distally-directed projection comprises a tubular member within a surrounding distal portion of the detachable device lumen valve, the surrounding distal portion having internal threading to mate with external threading provided on the hemostatic safety valve.

13. The system of claim 11, wherein the hemostatic safety valve has a proximal tubular portion with the external threading, and wherein the elastomeric valve member extends on the outside of and occludes the proximal end of the proximal tubular portion.

14. The system of claim 11, wherein the elastomeric valve member of the hemostatic safety valve is a slit valve.

* * * * *

UNITED STATES PATENT AND TRADEMARK OFFICE
CERTIFICATE OF CORRECTION

PATENT NO. : 6,592,544 B1
DATED : July 15, 2003
INVENTOR(S) : Charles R. Mooney and Clifford E. Currier It is certified that error appears in the above-identified patent and that said Letters Patent is hereby corrected as shown below:

Column 3,
Line 19, after "include" please delete "ajunction" and insert -- a junction. --

Column 4,
Line 7, after "the" please delete "44" and insert -- 4—4. --

Column 13,
Line 64, after "with" please delete "ajunction" and insert -- a junction. --

Column 14,
Line 9, after "syringe 636" please delete "maybe" and insert -- may be. --
Line 42, after "having" please delete "ajunction" and insert -- a junction. --
Line 43, after "thereof" please insert a period -- . --.
Line.56, after "thereof" please insert a period. --. --.

Column 16,
Line 30, after "will" please delete "filly" and insert -- fully. --.

Column 18,
Line 40, after "of " please delete "ajunction" and insert -- a junction. --

Column 19,
Line 56, after "housing" please delete "824by" and insert -- 824 by. --
Line 64, after "of " please delete "ajunction" and insert -- a junction. --

Signed and Sealed this

Twenty-seventh Day of April, 2004

JON W. DUDAS
*Acting Director of the United States Patent and Trademark Office*